US008048278B2

(12) United States Patent
Broadley et al.

(10) Patent No.: US 8,048,278 B2
(45) Date of Patent: *Nov. 1, 2011

(54) REFERENCE ELECTRODE HAVING A FLOWING LIQUID JUNCTION AND FILTER MEMBERS

(75) Inventors: Scott T. Broadley, Mission Viejo, CA (US); Herbert P. Silverman, Laguna Beach, CA (US); Ta-Yung Chen, Lake Forest, CA (US); Steven R. Ragsdale, Mukilteo, WA (US)

(73) Assignee: Broadley Technologies Corporation, Irvine, CA (US)

( * ) Notice: Subject to any disclaimer, the term of this patent is extended or adjusted under 35 U.S.C. 154(b) by 905 days.

This patent is subject to a terminal disclaimer.

(21) Appl. No.: 11/925,658

(22) Filed: Oct. 26, 2007

(65) Prior Publication Data

US 2008/0099336 A1    May 1, 2008

Related U.S. Application Data

(63) Continuation of application No. 10/613,976, filed on Jul. 2, 2003, now Pat. No. 7,344,627, which is a continuation-in-part of application No. 10/361,708, filed on Feb. 6, 2003, now Pat. No. 7,025,871, and a continuation-in-part of application No. 09/738,881, filed on Dec. 14, 2000, now Pat. No. 6,616,821, and a continuation-in-part of application No. 09/590,781, filed on Jun. 8, 2000, now Pat. No. 6,599,409, said application No. 10/361,708 is a continuation of application No. 09/590,781, said application No. 09/738,881 is a continuation-in-part of application No. 09/590,781.

(60) Provisional application No. 60/138,141, filed on Jun. 8, 1999, provisional application No. 60/394,106, filed on Jul. 3, 2002.

(51) Int. Cl.
*G01N 27/401* (2006.01)
(52) U.S. Cl. .......................................... 204/435; 205/775
(58) Field of Classification Search .................. 204/416, 204/435; 205/775
See application file for complete search history.

(56) References Cited

U.S. PATENT DOCUMENTS 2,595,042  A    4/1952  Wyllie
(Continued)

FOREIGN PATENT DOCUMENTS

DE         12 17 657  B    5/1966
(Continued)

OTHER PUBLICATIONS

Brezinski, Donald, *Kinetic, static and stirring errors of liquid junction reference electrodes*, Corning Glass Works, Apr. 1983: vol. 108, No. 1285, pp. 425-442.

(Continued)

*Primary Examiner* — Kaj K Olsen
(74) *Attorney, Agent, or Firm* — Knobbe Martens Olson & Bear LLP

(57) ABSTRACT

A flowing junction reference electrode comprising a liquid junction member matched with a filter. The junction member and the filter are situated between a reference electrolyte solution and a sample solution. An array of nanochannels spans the junction member and provides fluid communication between the electrolyte solution and the sample solution. The filter is configured to allow a greater flux of electrolyte than that associated with the junction member. Preferably, the number of pores is greater than the number of nanochannels. The filter is preferably configured to have pores with an inner diameter that is the same or less than the inner diameter of the nanochannels. In some embodiment, the resistance of the filter is made lower relative to the resistance of the junction member by selecting suitable length, number, and inner diameter size for the pores of the filter relative to the nanochannels of the junction member.

14 Claims, 24 Drawing Sheets

U.S. PATENT DOCUMENTS

| | | | |
|---|---|---|---|
| 3,410,779 A | 11/1968 | Whitehead, Jr. et al. |
| 3,445,368 A | 5/1969 | Detemple |
| 3,463,717 A | 8/1969 | Koopman et al. |
| 3,528,904 A | 9/1970 | Cliffgard |
| 3,607,702 A | 9/1971 | Haller |
| 3,677,844 A | 7/1972 | Fleischer et al. |
| 3,756,936 A | 9/1973 | Neuwelt |
| 3,915,829 A | 10/1975 | Krebs |
| 3,917,523 A | 11/1975 | Stein et al. |
| 3,926,765 A | 12/1975 | Haddad |
| 4,002,547 A | 1/1977 | Neti et al. |
| 4,012,308 A | 3/1977 | Jerrold-Jones et al. |
| 4,177,126 A | 12/1979 | Imaki et al. |
| 4,366,040 A | 12/1982 | Marsoner et al. |
| 4,495,052 A | 1/1985 | Brezinski |
| 4,592,824 A | 6/1986 | Smith et al. |
| 4,818,366 A | 4/1989 | Yonco et al. |
| 4,886,505 A | 12/1989 | Haynes et al. |
| 5,264,722 A | 11/1993 | Tonucci et al. |
| 5,304,487 A | 4/1994 | Wilding et al. |
| 5,360,529 A | 11/1994 | Edwards et al. |
| 5,397,452 A | 3/1995 | Buck et al. |
| 5,632,876 A | 5/1997 | Zanzucchih et al. |
| 5,641,808 A | 6/1997 | Gaffney et al. |
| 6,165,336 A | 12/2000 | Maki et al. |
| 6,495,012 B1 | 12/2002 | Fletcher et al. |
| 6,599,409 B1 | 7/2003 | Broadley et al. |
| 6,616,821 B2 | 9/2003 | Broadley et al. |
| 7,005,049 B2 | 2/2006 | Broadley et al. |
| 2001/0045357 A1 | 11/2001 | Broadley et al. |
| 2002/0189943 A1 | 12/2002 | Fletcher et al. |
| 2003/0168354 A1 | 9/2003 | Broadley et al. |
| 2003/0178305 A1 | 9/2003 | Catalano et al. |
| 2004/0011670 A1 | 1/2004 | Broadley et al. |
| 2004/0195098 A1 | 10/2004 | Broadley et al. |

FOREIGN PATENT DOCUMENTS

| | | |
|---|---|---|
| EP | 0 761 094 A1 | 3/1997 |
| FR | 25414624 | 8/1984 |
| GB | 2 093 193 A | 8/1982 |
| JP | 08-285811 | 1/1996 |
| JP | 10104193 A2 | 4/1998 |
| JP | 11258197 A1 | 9/1999 |
| WO | WO 99/63334 A1 | 12/1999 |
| WO | WO 01/75430 A2 | 10/2001 |

OTHER PUBLICATIONS

Covington, et al., *Improvements in the precision of pH measurements of a laboratory reference electrode with renewable free-diffusion liquid junction*. Analytica Chemical Acta, 169 (1985) 221-229.

Dohner, at al., *Reference electrode with free-flowing free-diffusion liquid junction*, Analytical Chemistry, vol. 68, No. 12 (1986) pp. 2585-2589.

Hulteen, J.C. et al., *A general template-based method for the preparation of nanomaterials*, J. Matr. Chem. 7(7): (1997) pp. 1075-1087.

Illingworth, John, *A common source of error in pH measurements*, Biochem. J. (1981) 195, 295-262.

Nishizawa, M. et al., *Metal nanotubule membranes with electrochemically switchable ion-transport selectivity*; Science, American Assoc. for the Advancement of Science, 268, 700-702 (1995).

Peters, G., *A Reference Electrode with free-diffusion liquid junction for electrochemical measurements under changing pressure conditions*; Analytical Chemistry, US American Chemical Society: 69:13 2362-2366 (1997).

Suzuki, et al., *Microfabricated Liquid Junction Ag/AgCl Reference Electrode and Its Application to a One-Chip Potentiometric Sensor*, Anal. Chem. vol. 71, No. 22, pp. 5069-5075, (1999).

Office Action issued on Aug. 13, 2010, from U.S. Appl. No. 11/925,665.

US 6,425,995, 07/2002, Fletcher et al. (withdrawn)

FIG. 6
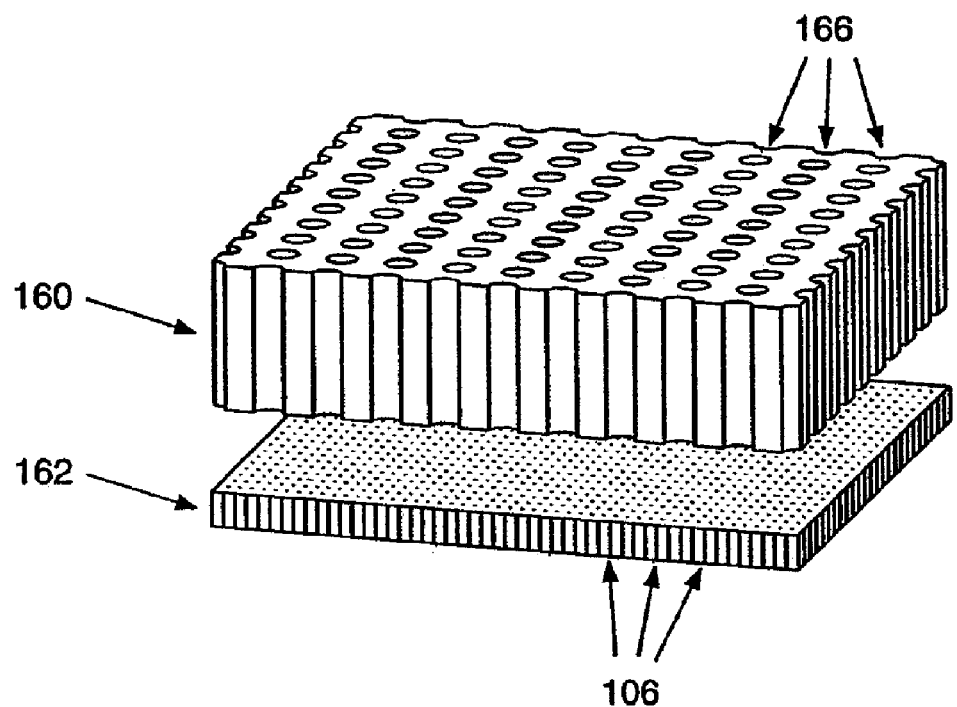
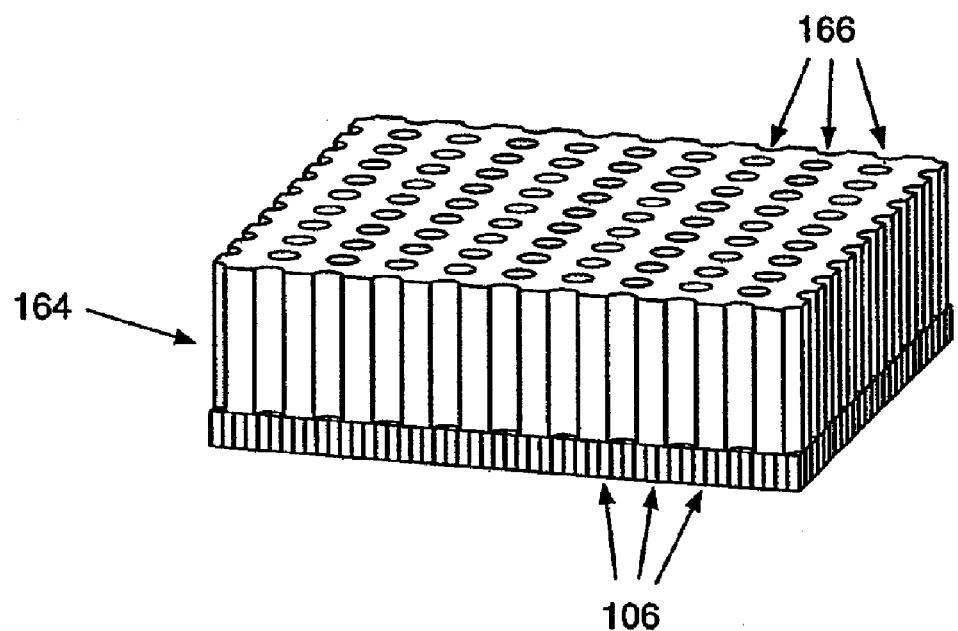

REFERENCE ELECTRODE HAVING A FLOWING LIQUID JUNCTION AND FILTER MEMBERS

PRIORITY CLAIM AND RELATED APPLICATIONS

This application hereby incorporates by reference herein, U.S. application Ser. No. 09/590,781, filed Jun. 8, 2000, issued as U.S. Pat. No. 6,599,409 on Jul. 29, 2003; U.S. application Ser. No. 09/738,881, filed Dec. 14, 2000, issued as U.S. Pat. No. 6,616,821 on Sep. 9, 2003; U.S. application Ser. No. 10/361,708, filed Feb. 6, 2003, issued as U.S. Pat. No. 7,025,871 on Apr. 11, 2006; U.S. application Ser. No. 10/613,976, filed Jul. 2, 2003, issued as U.S. Pat. No. 7,344,627 on Mar. 18, 2008; U.S. Application Ser. No. 60/138,141, filed Jun. 8, 1999; and U.S. Application Ser. No. 60/394,106 filed Jul. 3, 2002.

This application is a continuation of U.S. application Ser. No. 10/613,976, filed Jul. 2, 2003, issued as U.S. Pat. No. 7,344,627 on Mar. 18, 2008. U.S. application Ser. No. 10/613,976 is a continuation-in-part of U.S. application Ser. No. 10/361,708 (filed Feb. 6, 2003, issued as U.S. Pat. No. 7,025,871 on Apr. 11, 2006). U.S. application Ser. No. 10/613/976 is a continuation-in-part of U.S. application Ser. No. 09/738,881 (filed Dec. 14, 2000, issued as U.S. Pat. No. 6,616,821 on Sep. 9, 2003). U.S. application Ser. No. 10/613,976 is a continuation-in-part of U.S. application Ser. No. 09/590,781 (filed Jun. 8, 2000, issued as U.S. Pat. No. 6,599,409 on Jul. 29, 2003). U.S. application Ser. No. 10/361,708 is a continuation of U.S. application Ser. No. 09/590,781 now U.S. Pat. No. 6,599,409, filed Jun. 8, 2000. U.S. application Ser. No. 09/738,881 is a continuation-in-part of U.S. application Ser. No. 09/590,781 now U.S. Pat. No. 6,599,409 filed Jun. 8, 2000. U.S. application Ser. No. 09/590,781 (filed Jun. 8, 2000) claims priority to U.S. Provisional No. 60/138,141 (filed Jun. 8, 1999). U.S. application Ser. No. 10/613,976 claims the benefit of U.S. Provisional No. 60/394,106, filed Jul. 3, 2002.

This invention was made with United States Government support under SBIR Phase I and Phase II Grant Nos. DMI-9960665 and DMI-0110520 awarded by the National Science Foundation. The United States Government has certain rights in this invention.

BACKGROUND OF THE INVENTION

1. Field of the Invention

The invention relates to potentiometric and electrochemical reference electrodes and, in particular, to composite liquid junction structures such as to be used in electrochemical reference electrodes for electrochemical measurements of solutions. The invention more particularly relates to reference electrodes for use where measurement or control of potential is desired such as with pH or ISE potentiometric sensors used for laboratory analysis, for on-line process monitoring, for field measurements, or in any application where the improved precision or extended useful life of the sensor is desirable. The invention also relates to, and may also be used, in non-potentiometric applications to be carried out at fixed potentials such as, for example, electrochemical machining and electro-organic synthesis.

2. Description of the Related Art

The invention is broadly concerned with reference electrodes, such as the reference electrode portion of combination electrodes, and the reference portion of all potentiometric devices that employ a reference electrode to provide the relatively stable reference potential required in various measurements such as electroanalytical measurements, controlled potential coulometry, polarography, and the like.

Potentiometric measurements are used widely for the determination of pH and the detection of other specific ions in a variety of settings, including chemical processes, environmental monitoring, health care and bio-processes. The accuracy of these measurements depends on the ability to measure the potential difference between a sensing electrode, whose potential varies with the analyte concentration in the measured sample solution, and a reference electrode, which ideally would maintain a constant potential. The physical interface between the reference electrode (typically the electrolyte of the reference electrode) and the sample solution is referred to as the liquid junction. The stability of the reference electrode, and consequently the accuracy of potentiometric measurements, are dependent on the constancy of the liquid junction and more particularly, the constancy of the potential across the liquid junction. However, the liquid junction and more particularly, the potential across the liquid junction are difficult to control and maintain at a constant level. Typically, it is the change in the liquid-junction potential that introduces error into the electrochemical measurement and results in the need for frequent sensor system calibration.

The errors observed in currently commercially available reference electrodes include transient or kinetic error, static error, and stirring error. Transient or kinetic error may arise from and typically refers to the relatively slow response between measurements, and slow ability to reach equilibrium, typically of five, ten, or fifteen minutes after exposure to extreme solutions. This delayed response is primarily caused by entrapment of sample solution within the physical junction. Transient error is typically a function of the time required to disperse this entrapped layer of sample solution and obtain a direct interface. The extent of this error is determined by the duration of prior immersion. Static errors may arise from and typically refer to persistent offset after equilibrium is reached. Large static errors are typically caused by irreversible entrapment of sample solution deep within the physical junction structure. Stirring error may arise from and typically refers to the shift in potential due to or associated with agitation of the sample solution. Stirring error is typically observed where there is a rate of agitation or flow of the sample. These errors exist in potentiometric electrode measurements of sample solutions, but tend to be suppressed in standard buffers where electrode accuracy is being checked. Therefore, users may see no reason to disbelieve the erroneous readings obtained in non-standard solutions. See D. P. Brezinski, "Kinetic, Static, and Stirring Errors of Liquid Junction Reference Electrodes", Analyst 108 (1983) 425-442; see also U.S. Pat. No. 4,495,052. These errors are large enough to be of practical consequence, and often correspond to relatively large difference in hydrogen ion (H+) concentration or activity. These errors, including those errors described above, tend to bias the measurements observed on pH meters by as much as 0.5 pH unit.

In typical, currently commercially available electroanalytical measurement systems, the interface between the reference electrode's electrolyte and the sample solution is the liquid junction. The junction potential at this sample-reference interface is related to a number of factors; it is an object of every reference electrode design to minimize the effect of the factors that would cause the liquid junction potential to drift or to vary in any way over time. Various materials have been utilized in forming a liquid junction, including porous ceramic rods, porous polymer disks, wood dowels, ground glass sleeves, capillary tubes, agar gels, asbestos fiber bundle, and other porous materials or devices, and the like. These junction structures are, in general, referred to as restriction devices because their function is to restrict the outward flow or diffusion of electrolyte from the reference electrode. However, one important factor that limits the useful lifetime of a reference electrode is that junction structures typically allow the sample solution to enter the junction structure. This transport of sample solution into the junction, whether by diffusion, migration, convection or other mechanism, results in the contamination of the junction structure and a resultant undesirable variation in the liquid junction potential. Such variation typically necessitates re-calibration of the electroanalytical measurement system. If this type of contamination of the junction continues over time, the junction structure may become fouled or clogged and develop even larger offset potentials and/or potentials that chronically drift despite repeated attempts at re-calibration. In addition, sample solution will often transport past the junction structure and reach the reference half-cell itself, potentially causing additional adverse reactions.

Currently commercially available reference electrodes, especially those used for potentiometric measurements, are typically constructed based on one of two distinct designs. Each of these designs is meant to address one principle limitation encountered when using reference electrodes for making potentiometric measurements. However, each of these designs fails to address a distinct principle limitation encountered when using reference electrodes for making potentiometric measurements.

One design category is often referred to as a flowing junction reference electrode. This design provides a stream of reference electrolyte flowing through a porous junction structure or member, in an attempt to provide a relatively uniform liquid junction potential. While this design is typically effective in providing a liquid junction potential that is more uniform over time than those of the alternate design, flowing junction reference electrodes typically require the use of large amounts of electrolyte over relatively short periods of time. Thus, currently commercially available flowing junction reference electrodes require frequent maintenance to replenish the supply of this electrolyte solution. Furthermore, while flowing junctions are often designed to minimize this use of electrolyte by restricting the volumetric flow of electrolyte, in such flowing junctions designs the flow velocity is often reduced to a velocity that is sufficiently low enough so that the sample solution enters the liquid junction structure, typically via mass transport (diffusion, migration, or convection). The presence of this sample solution in the junction structure causes variable junction potentials, loss of calibration, clogging of the junction structure, and, over time, failure of the reference electrode. See U.S. Pat. No. 5,360,529.

The alternative design category is referred to as a non-flowing, diffusion junction reference electrode. This design depends on the substantially constant diffusion of electrolyte solution through a minimally porous junction structure to provide a steady liquid junction potential. While this design is highly susceptible to mass transport of the sample stream into the porous structure, the resulting drift in liquid junction potential may be slow enough to be tolerable in certain industrial applications. While such electrodes require frequent re-calibration, they do not require replenishment of electrolyte to the extent that flowing liquid junction electrodes do. Furthermore, such electrodes do not require systems and associated equipment to feed the reference electrolyte to the electrode, as is the case for typical flowing liquid junction electrodes.

Both reference electrode designs are in wide use but, based on their respective limitations, are typically used in different areas of application. Where precision measurements are more often needed, the flowing liquid junction reference electrode is typically used. Thus the flowing junction design is most commonly used for laboratory reference electrodes and clinical analyzers. In the laboratory environment the reference electrolyte may be relatively easily refilled as needed, even on a relatively frequent basis. Where it is desirable to minimize maintenance and where precision may be sacrificed to certain degrees, the diffusion junction reference electrode is more often utilized. Thus the diffusion junction reference electrode is typically used in industrial potentiometric sensor designs. An industrial sensor that uses a non-flowing, diffusion junction reference will typically require re-calibration on a more regular basis because of the relatively large amount of transport of the sample stream into the liquid junction structure. It is therefore not unusual for the industrial operator to install a new sensor every three months instead of attempting to re-calibrate the old sensor. For this reason, the industrial pH sensor with a built-in diffusion reference electrode is now a disposable item in most industrial applications.

In summary, two principal problems with currently commercially available reference electrodes are the frequent maintenance requirement of the flowing junction design electrodes and the frequent re-calibration requirements of the diffusion junction design electrodes. More specifically, nearly all flowing junction designs consume large amounts of electrolyte and this electrolyte needs to be replenished on a regular basis. While there are a few flowing junction designs that require small amounts of electrolyte, these designs have achieved this by greatly reducing the electrolyte flow to the point that the sample solution flows into the liquid junction structure. A slow flowing junction reference electrode performs little better than a non-flowing, diffusion junction reference electrode. On the other hand, the non-flowing, diffusion junction electrode requires no electrolyte replenishment but will be subject to slow drift errors due to transport of the sample stream into the liquid junction structure. This drift typically prevents such reference electrodes from being used for precision measurements. Frequently, such transport will cause an irreversible instability to develop in the reference electrode that will render it incapable of being re-calibrated. Because of these inherent shortcomings, sensors employing such reference electrodes are often designed to be thrown away and replaced instead of re-calibrated. As a group, all non-flowing, diffusion junction reference electrodes have a very short operational life measured in weeks and months and in the best of circumstances seldom over one to two years.

Accordingly, there is a need in the art for an electrode design that exhibits both the relatively stable potential of currently commercially available flowing junction designs and the relative lack of the need to replenish reference electrolyte solution as found in currently commercially available non-flowing junction designs. Such a needed design would exhibit a relative stable junction potential over prolonged periods of time, while not exhibiting the various limitations and drawbacks of currently commercially available flowing junction and non-flowing designs.

SUMMARY OF THE INVENTION

A microfluidic flowing liquid junction member, for use in a variety of potentiometric devices such as reference electrodes or combination electrodes, is described. This microfluidic flowing liquid junction comprises nanochannels in a microfluidic structure that creates a substantially invariant liquid junction potential. The microfluidic flowing liquid junctions comprising nanochannels in a microfluidic structure also preferably exhibit resistances across the junction member that are less than approximately 100, 10, 5, 2 or 1 MO. Low volume of flow through the array of nanochannels, and high velocities of electrolyte may be employed to prevent back diffusion of sample solution into the junction structure. Prevention of such back diffusion increases the precision and useful life of a reference electrode having the described junction member. The microfluidic flowing liquid junction member is useful to construct highly stable, low maintenance, precision electrochemical sensors, including reference electrodes.

A flowing junction reference electrode exhibiting such heretofore unattainable characteristics is described structurally as comprising a composite microfluidic liquid junction member that is situated between a reference electrolyte solution and a sample solution. This microfluidic liquid junction member has an array of nanochannels spanning the member and physically connecting the reference electrolyte solution and a sample solution. The reference electrolyte solution flows through the array of nanochannels and into the sample solution at a linear velocity, and the sample solution does not substantially enter the array of nanochannels. The sample solution does not substantially enter the array via any mass transfer mechanisms such as diffusion, migration, and convection. A sample solution that enters the array at a rate of less than approximately $2 \times 10^{-9}$ moles per day, and preferably less than approximately $1 \times 10^{-9}$ moles per day, should be considered as not substantially entering the array. The number of nanochannels in the array is preferably between approximately $10^8$ and approximately 10, more preferably less than approximately $10^6$, less than approximately $10^5$, and less than approximately $10^4$, and most preferably between approximately $10^4$ and approximately 100. The number of nanochannels may also be, less preferably, between approximately 10 and approximately 1000, including approximately 10, approximately 40, approximately 100, approximately 200, approximately 400, and approximately 800. Also preferably, the nanochannels are substantially straight and are substantially parallel to one another; such an array of nanochannels is herein described as anisotropic. The nanochannels are also preferably coated, and may be coated with, for example, metals, alloys, hydrophilic materials, or hydrophobic materials. The widths of any nanochannels in the array of nanochannels are preferably substantially uniform, in that the width of any nanochannel is substantially equal to the width of any other nanochannels in the array. The nanochannels preferably have widths of greater than approximately 1 nanometer and less than approximately 900 nanometers, more preferably greater than approximately 10 nanometers and less than approximately 500 nanometers, and preferably between about 200 and about 300 nanometers. The junction structure may be constructed out of any suitable material, and is preferably constructed of a polymer, most preferably the polymer is selected from the group consisting of polycarbonate and polyimide, and may also be constructed of other structurally strong polymers, silicon, glass, or ceramic.

The electrode may also further comprise a pressurized collapsible bladder, an electro-osmotic pump, or other mechanical pump, or any other means for maintaining positive linear flow of the reference electrolyte solution through the array of nanochannels and into the sample solution. The disclosed reference electrode may be used as part of a combination electrode along with an appropriate sensing electrode such as a pH electrode, an ion-selective electrode, a redox electrode, or the like.

A flowing junction reference electrode exhibiting such heretofore unattainable characteristics may also be described as comprising a reference electrolyte solution flowing through a junction member and into a sample solution; wherein substantially no sample solution enters into the junction member via mechanisms of mass transfer such as diffusion, migration, or convection mechanisms. The linear velocity of the reference electrolyte solution flowing into the sample solution is preferably greater than approximately 0.1 cm per second, more preferably greater than approximately 0.5, and more preferably greater than approximately 1.0 cm per second. The volumetric flow rate of the reference electrolyte solution into the sample solution is less than approximately 60 µL per hour, and more preferably less than approximately 10 µL per hour. The microfluidic flowing liquid junction reference electrode is capable of having a lifetime of greater than one year, and preferably greater than two, three, four, five, or ten years, during which variations of electrolytic potential are less than approximately 1 mV per year, and during which less than approximately 100 ml of electrolyte flows into the sample solution, and more preferably less than approximately 50 ml. The resistance across the junction member is preferably less than approximately 100, 10, 5, 2 or 1 MO.

Also disclosed is a microfluidic flowing junction reference electrode comprising one or more filter members together with a microfluidic liquid junction member having an array of discrete nanochannels. This combination may be referred to as an enhanced microfluidic flowing junction. Such an enhanced microfluidic flowing junction may comprise a first filter member having an array of pores; a microfluidic liquid junction member having an array of discrete nanochannels; wherein array of pores and the array of nanochannels are configured to allow a pressurized electrolyte solution to flow through the array of pores and the array of nanochannels and into a sample solution; wherein the junction member is positioned downstream from the first filter member, and wherein the electrolyte solution flows through the array of nanochannels at a linear velocity greater than about 0.1 centimeter per second, wherein the diameter of at least one pore in the array of pores is equal to or smaller than the diameter of at least one nanochannels in the array of nanochannels; wherein the number of pores in the array of pores is greater than the number of nanochannels of the array of nanochannels; and wherein the sample solution does not substantially enter the array of nanochannels. The first filter member having an array of pores may be a first filter member having an array of nanochannels, and those nanochannels may be, preferably, discrete and, even more preferably, substantially parallel, nanochannels.

The filter member may be any conventional filter configured to achieve the purpose of the electrode. Specifically, the filter should be capable of and permit at least a volumetric flow that is equal to or greater than the volumetric flow capacity of the junction and should serve to capture particles that would otherwise lodge in the junction. Accordingly, the filter member may be anisotropic or isotropic, may have uniform or varied pore sizes, may have discrete or interconnected pores, and should include at least some pores having an effective diameter equal to or smaller than the effective diameter of the nanochannels in the junction. In a preferred embodiment, at least one filter member comprises an anisotropic array of discrete nanochannels that serve as pores. An electrode comprising such a preferred electrode is configured such that the first array of nanochannels in the filter member and the second array of nanochannels in the junction member allow a pressurized electrolyte solution to flow through the first array and the second array and into a sample solution, and wherein the microfluidic flowing liquid junction is positioned downstream from the filter member, and further wherein the electrolyte solution flows through the second array at a linear velocity greater than about 0.1 centimeter per second.

The electrode may be further configured such that a typical diameter of the nanochannels of the first array is equal to or smaller than a typical diameter of the nanochannels of the second array, and wherein the number of nanochannels of the first array is greater than the number of nanochannels of the second array; and further wherein the sample solution does not substantially enter the second array.

BRIEF DESCRIPTION OF THE DRAWINGS

The accompanying drawings, which are incorporated in and constitute a part of the specification, are included herein to illustrate certain preferred embodiments of the invention and, together with the remainder of the written description and claims provided herein, including the Detailed Description of the Preferred Embodiments, serve to explain the principles of the invention. The accompanying drawings are not intended to limit or otherwise define the invention.

FIG. 6 depicts two schematic diametric views illustrating steps in the fabrication of a multi-planar layer polymer junction structure with anisotropic nanochannels and supporting microchannels.

DETAILED DESCRIPTION OF THE PREFERRED EMBODIMENT

Figure 1:
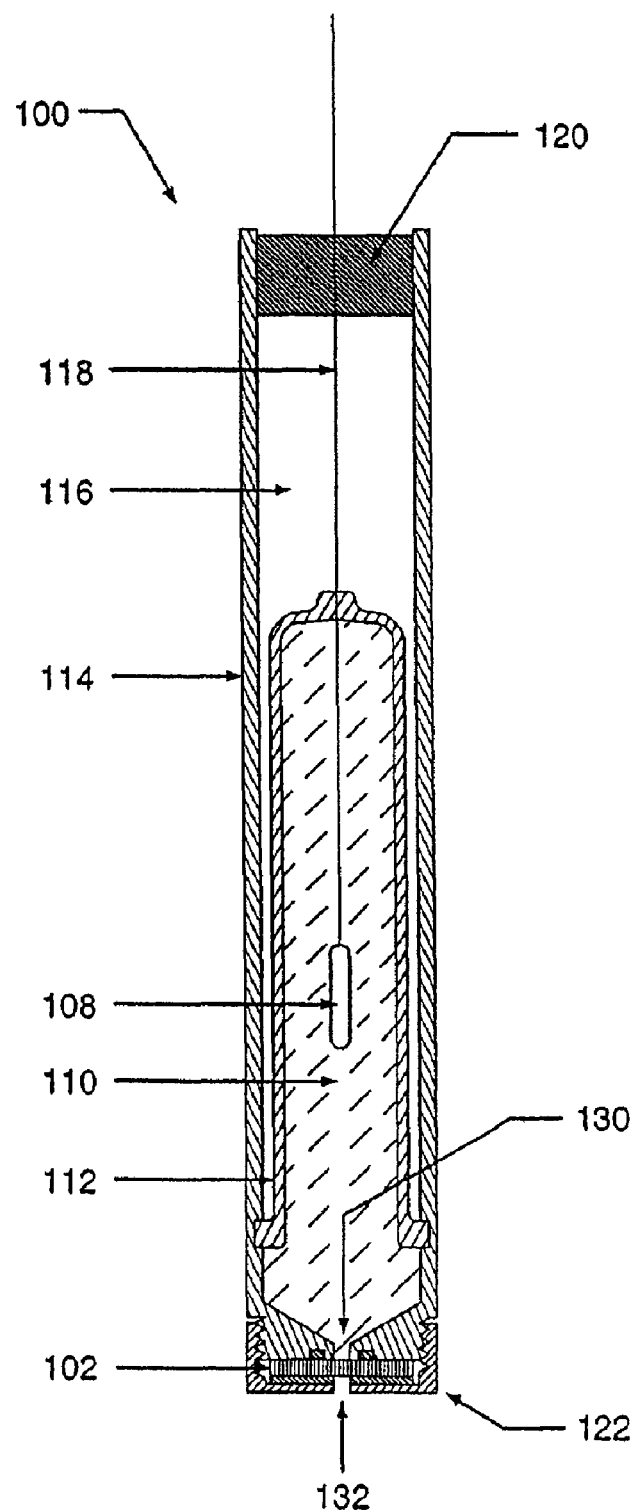
FIG. 1 depicts a schematic cross-sectional view of a reference electrode with means for holding the microfluidic flowing liquid junction in place at the end of the electrolyte reservoir.

A reference electrode is described that comprises a microfluidic flowing liquid junction having a well-defined junction region, said junction region containing a reference electrolyte, wherein said microfluidic liquid junction provides a linear rate of flow of said electrolyte that is adequate to suppress measurable changes in the electric potential of the junction for a period of at least one week, and preferably of longer periods including at least one month, at least three, six, and nine months, and at least one, one and one-half, two and as long as ten years. An electrochemical or potentiometric sensor is also described comprising a pH electrode, an ion-selective electrode, or redox electrode, and a reference electrode. The reference electrode comprising means for maintaining a liquid junction potential that remains stable for a period of at least one week, and preferably for longer periods including periods of at least one, two, three, six, or nine months, and at least one, one-and-one half, and two and as long as ten years.

By using a novel microfluidic junction structure having an array of nanochannels, it has been unexpectedly found that heretofore unattainably stable potentials, low junction potentials, and low electrolyte consumption rates for reference electrodes may be produced. These results are preferably attained by using combinations of the number of nanochannels and the nanochannel cross-section widths and a positive linear flow velocity for the reference electrolyte through the junction. The junction structure of the invention may therefore be characterized by, among other characteristics, (1) high electrolyte velocities to suppress transient, static, and stirring errors; (2) substantially constant junction potentials; (3) substantially constant potential despite the existence of volumetric flow rate and flow velocity fluctuations within the junction; (4) small junction potentials; (5) low junction resistance; and/or (6) extremely low consumption of electrolyte.

It is therefore one object of the invention to provide a reference electrode with a flowing liquid junction structure that will maintain a heretofore unavailable relatively constant, invariant, and fixed junction potential, such potential being maintained for extended periods of time, including periods of one month to up to one, two, three, and even ten years, without the need to replenish the reference electrolyte.

Another object of the invention is to provide a flowing liquid junction that functions for relatively prolonged periods of time on a relatively small amount of electrolyte and provides a substantially constant liquid junction potential that is substantially free of transient errors, static errors, and stirring errors.

It is another object of the invention to provide a reference electrode that will have minimal transient, static, or stirring errors in sample solutions of extreme pH solutions having relatively high concentrations of caustics or acids, and/or solutions having low ionic strength.

Another object of the invention is to provide a flowing liquid junction that is neither a "leak path" nor a "restricted diffusion" junction. In this flowing liquid junction of the invention, there is hydrodynamic transport across the junction structure or member into the sample solution. This hydrodynamic transport is preferably at a velocity sufficiently high to effectively counter back diffusion of the sample solution into the nanochannels of the junction. Prevention of this back diffusion contributes to the junction potential remaining stable and free of transient, static, and stirring errors for prolonged periods of time of one month to up to one, two, three, and even ten years.

Another object of the invention is to provide a flowing junction structure that provides a constant liquid junction potential over a broad range of electrolyte flow velocities. The liquid junction structure provides a constant potential that is relatively and substantially free of fluctuations even as the electrolyte velocity varies within various velocity ranges.

It is another object of the invention to provide a flowing junction reference electrode that functions for relatively long periods of time without the need for replenishment of the reference electrolyte or the associated maintenance. The reference electrode according to the invention may thus function for times of 1, 10, 20, 30, 40, 50, 60, 70, 80, 90 or even 100 years while using less than 100 ml of electrolyte.

It is another object of the invention to provide a flowing junction reference electrode that uses such small amounts of electrolyte that the electrode will consume as little as 1 ml of electrolyte per year. Certain preferred embodiments of the invention allow the reference electrode to function for as long as 10, 20, 30, 40, 50, or as long as 100 years on only 100 ml of electrolyte, or in other embodiments, less than a ml per week, a ml per month, or a ml per six months.

It is another object of the invention to provide a junction structure that comprises an array of nanochannels that provide electrolytic resistance as high as 100, 10, 5 2 or 1 MO. While each separate nanochannel is high in electrolytic resistance, the entire array of nanochannels provides a junction structure having an electrolytic resistance that is relatively low.

It is another object of the invention to provide a pressurized array of nanochannels that achieves a linear velocity of electrolyte necessary to substantially and effectively counter back diffusion of the sample stream into the junction and thus avoid transient, static, and stirring errors.

It is another object of the invention to provide a pressurized array of nanochannels that achieves a linear velocity of electrolyte necessary to substantially and effectively reduce fouling and blockage by gas bubbles or particulate matter.

It is another object of the invention to provide a pressure differential across the array of nanochannels, through which reference electrolyte flows. The volume of each typical nanochannel in the array is sufficiently small that high electrolyte velocity can be achieved for prolonged periods of time with the use of extremely small volumes of electrolyte. These prolonged periods of time can be as long as years and even decades.

It is another object of the invention to provide a reference junction structure sufficiently robust to function in a process industrial environment and sufficiently small to be incorporated as a basic building block into portable microfluidic module-based analytical devices.

It is another object of the invention to provide a liquid junction structure that can be miniaturized for compatibility and integration into microfluidic devices, such as for example hand-held analytic devices for use in remote locations, and portable analytic devices for use in field stations, battlefield hospitals, emergency stations or the like.

Another object of the invention is to produce a reference junction structure with a nanochannel array that may be manufactured with planar fabrication techniques so that the reference junction structure may be batch produced as an integral component of the various microfluidic structures and devices.

Another object of the invention is to provide a substantially invariant liquid junction structure that can be fully integrated into mesoscale and microscale microfluidic devices.

It is another object of this invention to provide a liquid Junction structure that can be miniaturized for compatibility and integration into microfluidic devices. A further, related object of this invention is to provide a liquid junction structure, the manufacture of which may be achieved through the use of current microfabrication techniques.

A device need not attain even one of these objectives to be within the scope of the invention.

General Discussion of the Uses and Design of Reference Electrodes

The microfluidic flowing liquid junctions and reference electrodes incorporating such microfluidic flowing liquid junctions, as disclosed herein, expand the use of electrochemical monitoring to remote and/or hazardous sites, and to in-line process conditions. Their use results in lower cost and improved efficiency of monitoring and controlling chemical and biological industrial processes. A reference electrode that extends the useful lifetime of a sensor and maintains a calibration for prolonged periods dramatically reduces maintenance requirements, increases efficiency, and decreases costs.

Reference electrodes are most typically used for example in the following way: In the measurements of ion concentration of solutions, a reference electrode is commonly employed in conjunction with a sensing electrode, such as a glass pH electrode, with both electrodes immersed in the test solution. The potential difference between the two electrodes is a function of the concentration of the specific ion in solution. A typical example is the conventional pH meter and pH electrode pair used for measuring hydrogen ion concentrations of solutions.

Reference electrodes are also frequently used in conjunction with an ion-sensing electrode such as a pH electrode, either separately or in combination, to measure the activity (which is a function of the concentration) of a given ion in a sample solution. The two electrodes, for example, the reference electrode and the pH electrode, both of which are immersed in the sample solution, typically are connected to a means of measuring the potential difference between the two electrodes, for example, an electrometer. The reference electrode is expected to provide a constant electromotive force or potential against which the potential of the ion-selective electrode is compared. The latter potential consists of a constant component from the electrochemical half-cell of the ion-selective electrode and a variable component which is the potential across the sensing membrane and which is dependent upon the activity (concentration) of the ion being measured. The variable component, then, is readily correlated with ion activity (concentration) by known means. To give accurate results, the potential of the reference electrode should not substantially change with the composition of the sample. Redox electrodes are used in conjunction with reference electrodes in a similar manner, as described above, to measure the oxidation-reduction potential of the solution.

When used in such applications, reference electrodes are meant to establish a relatively constant or stable potential, which in an ideal situation is independent of the composition of the liquid sample, but in practice varies with the liquid junction potential. The liquid junction potential is the potential difference, created across the interface between the sample solution and the reference electrolyte. This interface is typically present at the junction member. The junction potential will vary with varying dilution and varying ion composition between sample and electrolyte. These variations affect the measured results and they will become imprecise or misleading over time.

A reference electrode is typically comprised of an internal half-cell supported in a tube containing a salt solution, the tube of salt solution being known as a salt bridge. The salt bridge solution is a concentrated equitransferent salt solution such as potassium chloride or potassium nitrate. Ion flow between the salt solution and the sample or test solution is made by liquid flow through a suitably formed aperture or passage in a tube, generally referred to as the liquid junction structure or the leak structure. Sometimes the entire unit consisting of the internal half-cell structure, the tube, the salt solution, and the liquid junction structure is referred to as a half-cell; however, for the present specification, the entire unit will be referred to as a reference electrode.

Definitions

As used herein, the term "nanostructures" refers to assemblies that have dimensions in the range of approximately 1 to approximately 500 nm. Accordingly, "nanochannels" refer to channels having widths of approximately 1 to approximately 500 mm.

As used herein, the terms "mass transfer" and "mass transport" each refer to mechanisms for the flow of mass including diffusion, migration, and convection.

As used herein, the phrase "the sample solution does not substantially enter the array of nanochannels" refers to the substantial absence of back diffusion of the sample solution into the nanochannels of the junction where such back diffusion would measurably alter the potential of the reference electrode.

As used herein, the term "microfluidic" refers to a structure or device having channels or chambers which are generally fabricated at the micron or submicron scale. Such structures and devices preferably have at least one cross-sectional dimension in the range of about 10 nm to about 500 µm. Techniques commonly associated with the semiconductor electronics industry, such as photolithography, wet chemical etching, etc, are typically used in the fabrication of microfluidic structures. Such structures may be batch fabricated in, for example, silicon, polymers (including plastics), ceramic, glass, and quartz, using planar integrated circuit fabrication techniques.

As used herein, "fluid mechanics" refers to the study of motion and control of fluids. Micromachined fluid components offer the potential of revolutionizing applications where precise control of fluid flow is a necessity. Microfluidic systems comprising nozzles, pumps, channels, reservoirs, mixers, oscillators, and valves have been used in a variety of applications including drug dispensation, ink-jet printing, and general transport of liquids, gasses, and liquid/gas mixtures. The advantages of these devices include lower cost, enhancement of analytical performance, and lower consumption of reagents.

As used herein, the term "half-cell electrode" means the solid-phase, electron-conducting contact with the half-cell electrolyte, at which contact the half-cell oxidation-reduction reaction occurs which establishes the stable potential between the half-cell electrolyte and the contact. See, e.g., U.S. Pat. No. 4,495,052.

As used herein, the term "electrochemical" refers to any use and/or sensor that exploits electrochemistry; and includes within it the term "potentiometric."

As used herein, the terms "filter," "filter member," and "filtration member" are used interchangeably and refer to a structure made of permeable or semi-permeable material that allows passage through the structure to some particles but not others; the particles typically pass from one side of the structure to the other. It may be anisotropic or isotropic and may be constructed of various materials. For example, a filtration member may be a flat ceramic glass or polycarbonate disk having pores that prevent passage of particulates greater than a particular threshold, for example, 100 nm, while allowing smaller particulates to pass from one side of the disk to the other.

As used herein, the term "anisotropic," when used to refer to nanochannels, refers to nanochannels that are discrete, and are preferably substantially straight and are more preferably substantially parallel to one another.

As used here, the terms "pore" and "channel" are used interchangeably and refer to a passage that allows matter to pass through a structure such as a filtration member or a liquid junction structure.

As used here, the term "liquid junction" means the interface between two electrolyte solutions of different composition. Across such a junction there arises an electrical potential difference.

As used here, the term "volumetric flow rate" means the rate of transfer, per unit time, of a volume of electrolyte across a given surface.

As used here, the terms "linear flow rate" and "linear velocity" are used interchangeably and mean the velocity or speed, expressed as distance divided by time, of a solution, typically the electrolyte solution, as it traverses a point, typically along a pore or nanochannel, of a filtration member or a liquid junction structure.

As used here, the term "high flux filter" means a filtration member capable of allowing a flow rate of electrolyte that is much higher than that associated with a liquid junction structure used in conjunction with the filtration member in a reference electrode. The size of the inner diameter of the pore and the number of pores may be chosen such that the filtration member is capable of a much greater flux than the flux capability of the liquid junction structure with which the filtration member is used.

As used here, the terms "high capacity filter" and "high filtering capacity" refer to a filtration member having a sufficient number of pores that even after particulates clog a certain percentage of its pores, the flux capacity of the filtration member is nonetheless substantially greater than the flux capacity of a liquid junction structure used in conjunction with the filtration member in a reference electrode.

As used here, the term "high flux, high capacity filter" means a filtration member having both of the features described above.

As used here, the term "nanochannel array" means an anisotropic array of substantially parallel channels that traverse the plane of the array in a direction that is substantially perpendicular to the plane.

Manufacture of the Invention

Microfabrication of electrochemical sensors using integrated circuit (IC) technology has been challenged by the failure to incorporate a true reference electrode into the structure. See Mark Madou, "Fundamentals of Microfabrication," 1997, CRC Press, pg. 469. There is great potential for developing simple devices that are inexpensive, easy to fabricate, disposable, and highly sensitive. These devices can prove to be simple miniaturized diagnostic tools for various state-of-health indicators.

Back diffusion of sample solution into the physical junction generates a junction potential that not only shifts the calibration (generating static error) but may also cause the sensor signal to drift at any measurement point (generating transient error). Such back diffusion greatly increases the frequency of calibration required to obtain precise data from the electrochemical sensor. This increases the cost of ownership and places limits on the amount of time that such a device can function unattended. This is especially a problem for remote sensing devices that monitor water chemistry in lakes and streams and have a need to operate for extended periods of time without maintenance or recalibration.

Most attempts to minimize back diffusion require a flowing junction structure that needs large amounts of electrolyte and periodic refilling of the electrolyte reservoir and other associated maintenance. This adds to the operational complexity of the sensor device and increases the cost of ownership by requiring scheduled maintenance by a technician. This is especially a problem with remote environmental measuring devices that are deployed to monitor lake and stream water chemistry.

Volumetric and linear flow rate on the one hand, and electrolyte consumption on the other hand, are typically compromised one for the other. The volumetric flow rate is typically increased in order to increase the linear flow rate and, thereby, reduce back diffusion into the reference structure. However, increasing the flow rate has the detrimental effect of increasing the consumption of electrolyte. As stated above, it is therefore an object of this invention to provide a reference structure that prevents back diffusion while significantly increasing the linear velocity of the electrolyte flowing through the nanochannel array and minimizing volumetric flow rate. This velocity suppresses back diffusion of the sample into the reference structure and enables the reference electrode to be operated for extended periods of time without the need for recalibration.

Embodiments of the invention provide a junction structure that employs an array of nanochannels in a microfluidic structure to achieve a high electrolyte velocity while at the same time utilizing very low volumetric flow rates and using only sparingly small amounts of electrolyte solution. The microfluidic structure with its array of nanochannels can operate from 1 to 100 years on 100 ml of electrolyte. Alternatively a single milliliter of electrolyte could enable a small, disposable measurement device to operate with laboratory precision from 2 weeks to a year in harsh environments such as battlefield field hospitals.

Embodiments of the present invention substantially mitigate these long standing problems of reference junction stability and electrolyte consumption. With the embodiments of the present invention, potentiometric sensors systems can function for extended periods of time without the need for recalibration or electrolyte replenishment.

Embodiments of the present invention provide a microfluidic reference junction structure that enables precise potentiometric measurements to be made with devices and systems that operate remotely and without maintenance for long periods of time.

This reference structure can be miniaturized for compatibility and integration into microfluidic devices. Such miniaturization can be subject to performance and stability tradeoffs with existing junction structures. The microfluidic flowing liquid junction described herein achieves its superior performance because of its nanoscale structure. It is already small enough to be included as a subcomponent in a microscale device such as a disposable microfluidic chip, disk, or block. Yet the same microfluidic flowing liquid junction structure is robust enough to be readily utilized as the liquid junction of a macroscale industrial in-line sensor assembly or a mesoscale analytical handheld device.

A reference electrode with an substantially invariant liquid junction potential using an innovative combination of microfluidic and nanotechnology is described. The variability of the liquid junction potential is a significant factor in the accuracy of potentiometric measurements. Removing this variable will result in potentiometric measurements with improved stability, precision and reproducibility. A reference electrode with an substantially invariant liquid junction is capable of sustaining a stable potential. Reducing the calibration and maintenance will diminish the cost and enhance the ability to monitor remote and hazardous sites.

The reference electrode described herein preferably uses microfluidic concepts to incorporate a nanochannel array for the liquid junction structure. This microfluidic flowing liquid junction preferably maintains a constant potential reproducible to ±0.5 mV (~0.01 pH unit) and preferably has a life in excess of one year. An important factor is the stability of the liquid junction. In an electroanalytical system the interface between the reference electrolyte and the sample solution constitutes the liquid junction. Unless these two solutions have the same initial composition, the system will not be at equilibrium. Though the liquid junction region is not at equilibrium, if it has a composition that is effectively constant, then the reversible transfer of charge through the region can be considered. See Bard, A. J.; Faulkner, L. R. *Electrochemical Methods*; John Wiley & Sons: New York, 1980; pp. 61-64. Providing an adequate outward flow of junction electrolyte serves to suppress changes in the junction potential. See Brezinski, D. P. *The Analyst* 1983, 108, 425. Maintaining a constant composition, and narrow, well-defined liquid junction region, therefore protects the reference electrode's liquid-junction potential stability. The system uses small volumes of electrolyte to make it a practical device for operation for one year or more with a reduced level or no maintenance.

Factors that affect the liquid junction potential include temperature, ionic strength, ionic composition, and transport of ionic and molecular species across the reference structure. The most stable and reproducible reference electrodes use a flowing-liquid junction. The continuous flow of electrolyte maintains a constant rate of ion transport across the interface. In addition, the constant flow of electrolyte also prevents back diffusion of the sample into the reference electrolyte. However, a conventional flowing junction can use large quantities of electrolyte and require substantial maintenance, which is impractical in most industrial applications.

The microfluidic flowing liquid junction may be comprised of nanochannel arrays in a structure that results from recent developments in microfluidic and nanotechnology. This technology makes it possible to generate sufficient electrolyte flow through the liquid junction to eliminate contamination of the junction structure, yet use only minimal quantities of electrolyte. The microfluidic flowing liquid junction preferably maintains a constant potential for an extended duration of time, and preferably limits the volume of electrolyte to a volume rate of flow of less than 50 ml per year (6 µl per hour). This allows for reference electrodes, and consequently potentiometric or electrochemical sensors that require neither maintenance nor recalibration for periods of preferably at least one week, two weeks, one months, six months, or one year.

The feasibility of using the microfluidic flowing liquid junction, may be demonstrated by: (i) determining the electrolytic resistance across the nanochannel arrays; (ii) characterizing the flow of electrolyte through nanochannels as a function of applied pressure, nanochannel material, and nanochannel dimension, (iii) determining the required electrolyte velocity through a nanochannel to eliminate back diffusion of the sample solution into the reference electrode, and (iv) building a laboratory reference electrode and demonstrate a stable reference potential using a microfluidic flowing liquid junction.

Furthermore the microfluidic flowing liquid junction may be further optimized as follows: (i) optimizing the electrolyte velocity, nanochannel materials and dimensions, (ii) developing appropriate pumping mechanisms and designs.

The following description of the present invention is divided into two sections. The first section is a technical discussion of the microfluidic flowing liquid junction and its use in a reference electrode, including theoretical and conceptual discussions of the liquid junction and its potential, transport through microchannels, and the utility of nanochannel arrays. The second section lists and describes methods to achieve various tasks, including a discussion of the tests and experiments used to demonstrate the functionality of a microfluidic flowing liquid junction for a reference electrode.
A Reference Electrode Having a Microfluidic Flowing Liquid Junction Prototypes with a microfluidic flowing liquid junction are assembled in the following manner. The preferred junction has a modular design for easy exchange of different nanochannel arrays. The nanochannel array is sandwiched between two silicon rubber gaskets (an id of approximately 1 mm). The gaskets can be compressed and sealed to the electrode body. The electrode allows variable internal pressures. The reference electrolyte is forced to flow by applying a pneumatic pressure on the reference reservoir. The differential pressure is limited to 40 psig or to 100 psig. The reference reservoir contains approximately 50 ml of 4.0 M KCl, and uses a Ag/AgCl reference electrode.
Determination of the Electrolytic Resistance of the Nanochannel Array The electrolytic resistance of the nanochannel arrays is measured by AC impedance. A Solartron AC impedance system is available. The nanochannel array is clamped between the two halves of a U-tube permeation cell. Both half-cells are filled with 4.0 M KCl. The working and reference electrodes are placed in one half-cell (on one side of the array); the counter electrode is placed in the other half-cell (on the other side of the array). The impedance at high frequencies (e.g., 50 kHz to 100 kHz) is real and corresponds to the solution resistance. In this configuration, the solution resistance has three components; the resistance in one half-cell, the resistance in the second half-cell, and the resistance of the nanochannel array. The resistances of the half-cells are negligibly small relative to the nanochannel array resistance. This may be verified by repeating the same experiment without the array. If necessary, the measured solution resistance from this experiment will be subtracted from the measured resistance when the nanochannel array is in place. The measured resistances may be compared to calculated values obtained using eq. (3) below.

Characterizing the Electrolyte Volumetric Flow Rate and Linear Velocity

The flow rate and velocity of the reference electrolyte through the nanochannel arrays are determined as a function of applied pressure, nanochannel dimension, and nanochannel material. The applied differential pressure may be varied from 0 (diffusion) to 40 psi. The flow rate may be measured by placing the junction in 50 ml of ultra-pure water and measuring its transient conductivity. The experimentally determined flow rates may be compared to the predicted flow rates, calculated using eq. (2) below. The linear velocity may be calculated based on the pore density and dimensions of the nanochannel array.

The effect of charged nanochannel walls on the transport of the reference electrolyte may also be studied. Chloride ions readily adsorb on gold surfaces, thus, the Au nanochannels may have a net negative charge. In this situation, the nanochannels are cation permselective. However, if the nanochannels are pretreated with propanetbiol they have an inert, neutral coating, and chloride ions do not adsorb. To determine what effect charged walls may have on the transport, flow rates through Au nanotubules with negatively charged and neutral walls may be compared. This comparison provides useful information on the transport mechanism of permselectivity with pressure driven flow through nano-sized pores.

Measuring Back Diffusion as a Function of Linear Velocity of Electrolyte Solution Back diffusion as a function of velocity may be measured using a custom-designed pressure cell. Such a cell consists of feed and permeant half-cells. The feed half-cell will contain the 4.0M KCl. The permeant half-cell may be a dilute aqueous solution of a strongly absorbing dye molecule (e.g., Rhodamine B). The back diffusion of the dye from the permeant into the feed may be measured spectrophotometrically as a function of applied pressure. The rate of back diffusion may be measured by following the time-course of the dye appearance into the feed cell. The velocity of solution flow from the feed to the permeant may be measured by monitoring the conductivity of the permeant (due to transport of KCl from the feed) as a function of time. In this way, the minimum solution velocity (feed to permeant) required to eliminate back diffusion of dye (permeant to feed) into the reference electrode chamber will be determined.

Comparing Microfluidic Flowing Liquid Junctions to Standard Reference Junctions

A reference electrode having an microfluidic flowing liquid junction may be compared to traditional reference junctions to determine its relative potential and utility for reference electrodes. A reference electrode with a microfluidic flowing liquid junction may be used for pH measurements, and its response may be compared with different reference electrodes. The overall stability and performance of a reference electrode is determined from (i) transient error, (ii) static errors, and (iii) stirring errors.

First, when an electrode is transferred from one solution to another, if any of the first solution is retained within the liquid junction, the measured potential should have a contribution from the original solution. This is referred to as a memory effect, or transient error. Notwithstanding any permanent contamination, the liquid junction can be renewed by the continuous outflow of reference electrolyte. Memory effects, transient errors, may be determined by measuring the time required to achieve a steady potential response. The response times of the microfluidic flowing liquid junction may be compared with typical flowing, and diffusion-style reference junctions.

Second, stirring the sample solution can change the measured pH. Stirring can effect the potential measurement in at least two ways. Streaming potentials can build-up from convection of the sample solution. This becomes evident when the ionic concentration of the reference electrolyte differs from the sample, especially in low ionic strength sample solutions. In addition to streaming potentials, stirred sample solutions can increase contamination of the liquid junction.

The effect of pressure in the sample solution may be measured up to 40 psig, in or alternatively to 50, 60, 70, 80, 90, and 100 psig. The potential dependence of the microfluidic flowing liquid junction on temperature may then be determined.

Performance the Microfluidic Flowing Liquid Junction Over Extended Times

The microfluidic flowing liquid junction references may be placed in standard pH buffers for extended periods. The long-term testing may also be conducted in different media, including wastewater and soils. The microfluidic flowing liquid junction preferably retains its calibration to within 0.5 mV over a 24-hour period in adverse test conditions. However, a microfluidic flowing liquid junction preferably sustains a single calibration for even greater prolonged periods of time.

Certain Preferred Aspects of the Microfluidic Flowing Liquid Junction

Certain preferred aspects of the invention, many of which are further elucidated through the specific examples described herein and many of which may be observed in the various embodiments of the invention, are as follows:

According to a preferred aspect of the invention, there is provided an array of electrolyte flow channels in the junction member. As shown herein, an array, as opposed to a single channel lowers the overall junction resistance while minimizing electrolyte consumption. Each channel can be very high in resistance while the sum resistance of all the channels of an array will be several orders of magnitude lower in resistance. Without an array, or plurality, of channels the junction structure resistance would typically be too high for practical use.

According to another preferred aspect of the invention, there is provided an array of nanochannels in the junction member. Channels having internal diameters in the lower end of the nanometer range (for example, less than approximately 100 nm or approximately 70 nm) permit achieving the preferred elevated electrolyte solution linear velocity and the substantially constant liquid junction potential while consuming only relative small amounts of electrolyte solution. The array of nanochannels may also comprise approximately $10^3$, $10^4$, $10^5$, or $10^7$ nanochannels. The volume rate of flow is preferably less than approximately 50 ml per month, and may also be less than approximately 2 liters, 1 liter, 500 ml, 300 ml, 250 ml, 200 ml, 150 ml, or 100 ml per month, and more preferably less than approximately 50 ml per year, and may also be less than approximately 2 liters, 1 liter, 500 ml, 300 ml, 250 ml, 200 ml, 150 ml, or 100 ml per year. Also, the linear flow rate, dependent on the radii or effective width of the nanochannels employed, is preferably greater than approximately 0.1 cm per second, and, depending on the radii or effective width of the nanochannels, may be greater than 0.0001, 0.001, and 0.01 cm per second.

According to another preferred aspect of the invention, there are provided anisotropic channels in the junction member. Such channels are substantially straight and parallel to one another, and with uniform pore size provide substantially uniform distribution of flow through substantially all channels. Such channels may preferably be prepared according to the "template synthesis" method described herein and in Hulteen, J. C.; Martin, C. R. *J. Mater. Chem.* 1997, 7, 1075.

According to another preferred aspect of the invention, there are provided channels having internal diameters of less than approximately 100 nanometers or approximately 70, 50, 40, or 30 nanometers. Channels of these dimensions enable obtaining the preferred combination of electrolyte flow velocity, minimum electrolyte consumption, and array resistance.

According to another preferred aspect of the invention, there are provided channel lengths greater than approximately 100 nanometers and less than approximately ten microns. Channels at this dimension range (or smaller) also enable obtaining the preferred combination of electrolyte flow velocity, minimum electrolyte consumption, and array resistance.

According to another preferred aspect of the invention, there is provided a number of channels less than approximately one-hundred million ($10^8$). Arrays with fewer than this number of channels enable a desirable combination of electrolyte flow velocity, minimum electrolyte consumption, and array resistance.

According to another preferred aspect of the invention, there is provided a driven flow with high electrolyte velocity greater than approximately 0.1 cm/sec. Flow velocity is a factor in determining the preferred flow rate of electrolyte through the junction. Velocities at this rate or higher are preferred to substantially prevent penetration of each nanochannel by sample solution. Contrary to the commonly used technique of restricting the flow rate (volume and velocity) to minimize electrolyte consumption, preferred embodiments of the present invention increase velocity in a nanochannel structure while using relatively small amounts of electrolyte.

According to another preferred aspect of the invention, there is provided reduced volumetric consumption of electrolyte. Flowing junction designs traditionally use relatively large quantities of electrolyte and need frequent replenishment and associated maintenance. The design parameters of this reference junction provide superior electrolyte velocity with vastly reduced flow volume of reference electrolyte. For example, as little as one ml per year, is consumed under standard operating conditions. Preferred embodiments of the invention provide junction designs that can function for prolonged periods of time without the need for electrolyte replenishment and minimal contamination of the sample. Certain embodiments of this invention can, for example, operate up to 90 years with only 100 ml of electrolyte.

According to another preferred aspect of the invention, there is provided a low junction resistance: having a resistance across junction of less than approximately 100, 10, 5, 2, or 1 MO. The microfluidic flowing liquid junction electrode is shown to achieve high velocity and low volume electrolyte use without sacrificing junction resistance.

According to another preferred aspect of the invention, there is provided a junction that maintains a stable junction potential over a wide range of junction flow rates and flow velocities. Unexpectedly, the novel junction does not generate a different internal potential at different flow rates or flow velocities. Such a result is contrary to prior teachings. This unexpected property alleviates the need for maintaining a constant flow rate or velocity. Importantly, in a pressurized driven device, the flow rate will decrease as the electrolyte is depleted. Contrary to teachings and expectations, the junction potential has remained constant over a wide range of pressures and flow rates. For this reason, the electrolyte solution may be held in a flexible, pressurized collapsible bladder.

According to another preferred aspect of the invention, there is provided a reference electrode that may readily be integrated with any known variety of sensing electrode to make a combination sensor.

According to another preferred aspect of the invention, there is provided a combination sensor that may employ a battery powered compensating circuit. The circuit is designed to substantially null the inherent offset in the sensor and maximize the slope of the sensor response between two standards.

According to another aspect of the invention, it becomes unnecessary to maintain a constant pressure across the junction. The pressure may vary from high as 40 psig to as low as 10 psig and maintain substantially no error.

According to another aspect of the invention, various mechanisms may be used to maintain desired flow of electrolyte solution through the junction member. For example, a pneumatic driven flow or pump, such as a collapsible bladder, or electro-osmotic flow or pump or electro-hydrodynamic flow or pump may also be used. Also, for example, a mechanical pump or flow such as a piston-driven pump or flow may be used, or a spring-driven piston pump or flow, or a piezoelectric flow or pump or an electro-hydrodynamic flow or pumps may be used. Such pumps are well known in the art and are described by Marc Madou in "Fundamentals of Microfabrication", 1997, CRC Press, pg. 431-433.

According to another aspect of the invention, the inner walls of the microfluidic flowing liquid junction may be physically or chemically modified to alter the flow of electrolyte. For example, the inside walls of the structure may be coated with substances to enhance flow of electrolyte. Also, for example, the inside walls of the structure may be plated with metals such as gold, platinum, or palladium or another non-reactive metals or alloys or combinations thereof to increase functionality and to effect additional functionality or performance gains. Also, for example, the walls may be made hydrophilic by the addition of, for example, a hydrophilic polymer such as polyvinylpyrolidone (PVP). Alternatively, the walls may be made hydrophobic by the addition of a suitable hydrophobic material. Also a surfactant may be added to the electrolyte to alter the flow of electrolyte through the nanochannels, especially of the smaller nanometer structures.

In one embodiment, one or more surfaces of the liquid junction member have a coating comprising a biocide or growth inhibitor. The biocide may be, for example, an antibacterial or microbial agent. In one embodiment, the surfaces of the liquid junction are coated with butyl paraben. In some embodiments, the nanochannels are coated with the biocide or growth inhibitor. In other embodiments, only the surface of the liquid junction member in fluid communication with a sample solution is coated with the biocide or growth inhibitor. In some embodiments, the growth inhibitor coating includes a metal, e.g., copper.

In one embodiment of a combination electrode according to the invention, the electrolyte solution includes a biocide or growth inhibitor.

EXAMPLES

The microfluidic flowing liquid junction and associated electrodes of the invention are described in terms of several embodiments. These embodiments are preferred and comprise microfluidic liquid junction structures with nanochannel arrays fabricated from a variety of specific materials. Each preferred structure may be fabricated, according to techniques known in the art, into a thin wafer or membrane, preferably round, that can be mounted onto the end of a reference electrode structure. Each junction structure permits electrolyte flow through a nanochannel array from the internal electrolyte reservoir of the reference electrode into the sample solution.

FIG. 1 depicts a representative diagram of an exemplary potentiometric reference electrode 100 with a microfluidic liquid junction structure 102 according to the present invention. The reference electrode 100 comprises of a chamber 114 that has a seal 120 on one end and a compression means 122 for sealing the junction structure 102 in place at the other end. The reference electrode 100 includes an electrochemical half-cell 108, an electrical conductor 118, and a reservoir of reference electrolyte solution 110. The electrolyte reservoir 110 is contained in a flexible elastomer reservoir bag 112 that separates the electrolyte reservoir 110 from the compressed gas 116 that fills the rest of the chamber 114. The compressed gas 116 compresses the reservoir bag and the electrolyte therein and by this means drives the electrolyte 110 through the aperture 130 and into and through the microfluidic flowing liquid junction member and out the orifice 132 and into the sample stream (not shown). In this manner the reference electrode 100 shown in FIG. 1 utilizes the microfluidic flowing liquid junction structure 102 to make electrolytic contact between the internal electrochemical half-cell 108 and the sample solution (not shown).

Figure 2:
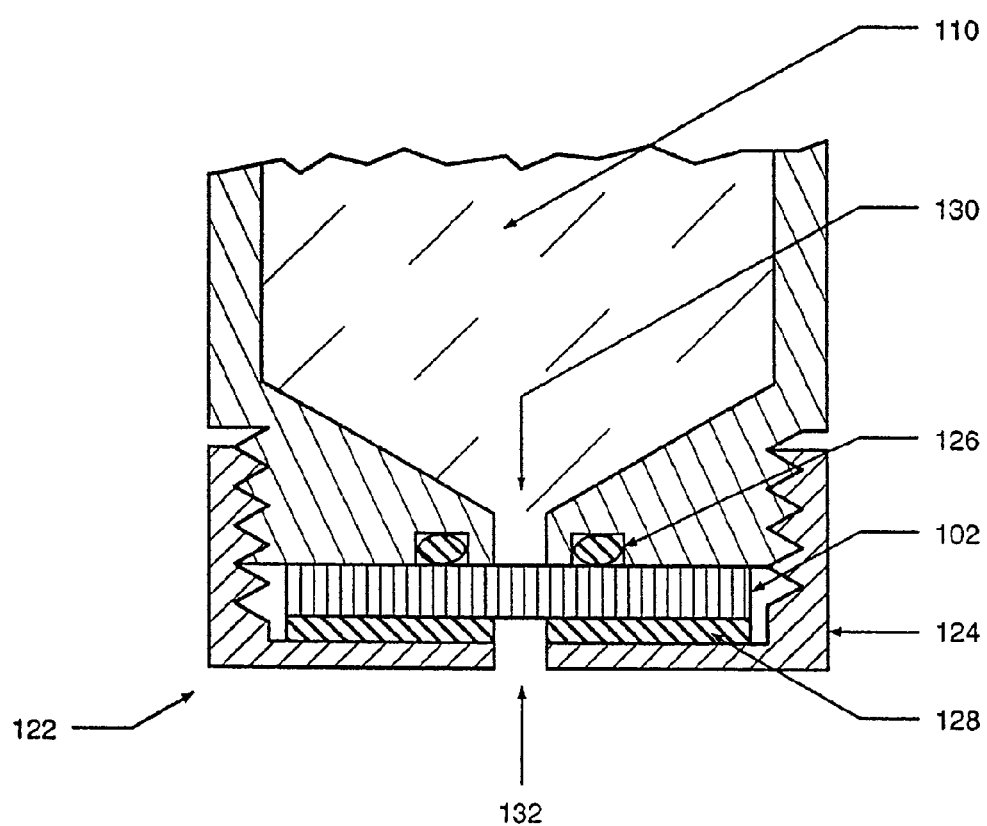
FIG. 2 depicts a detailed schematic cross-sectional view of a means for holding the microfluidic liquid junction structure in place.
Figure 3:
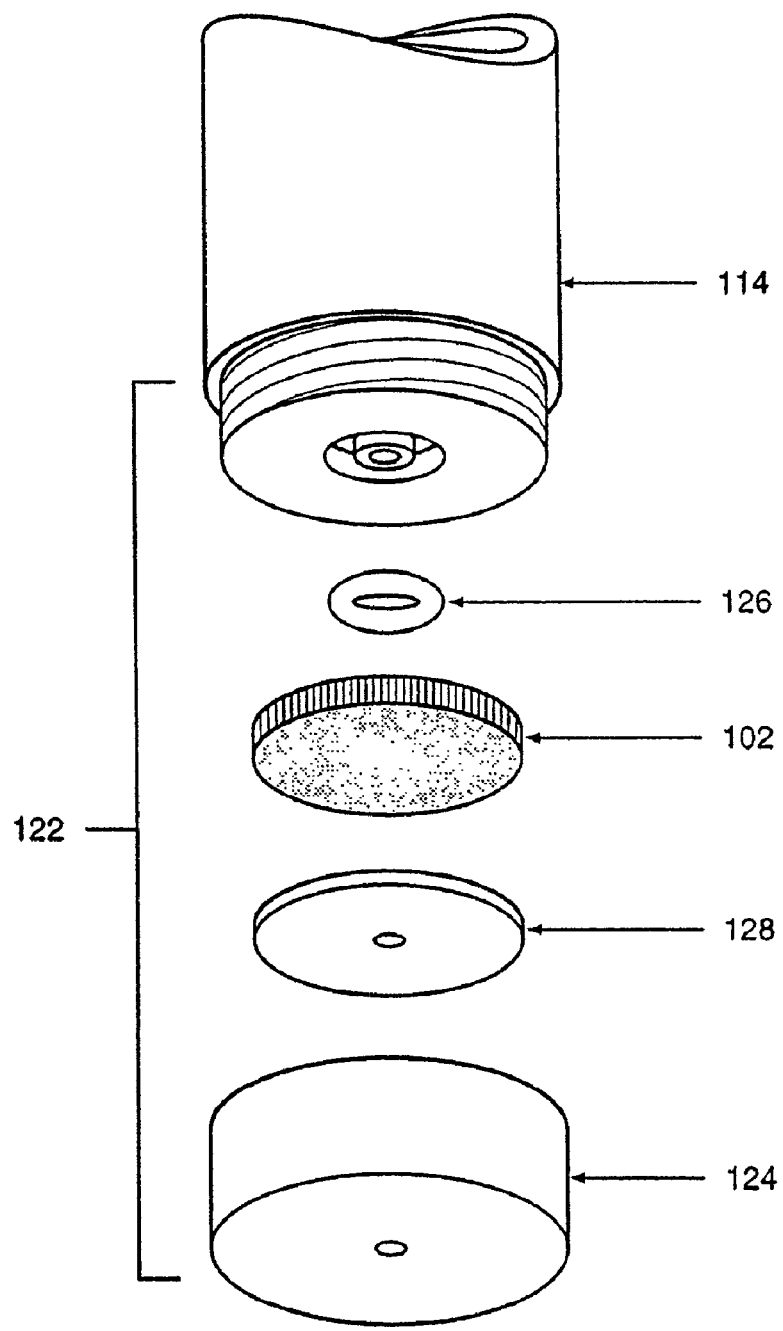
FIG. 3 depicts a schematic exploded diametric view of the means for holding the microfluidic liquid junction structure in place.

FIG. 2 depicts a cross-sectional view of the compression means 122 that seals the microfluidic liquid junction 102 structure onto the end of the reference electrode chamber 114, which chamber is shown in FIGS. 1 and 3. The threaded retainer ring 124 compresses the microfluidic liquid junction structure 102 against the o-ring 126 and the gasket 128 and thereby seals it into the end of the reference electrode chamber 114. The pressurized electrolyte 110 is pushed through aperture 130 and into and through the microfluidic liquid junction structure 102 then out of the orifice 132 and into the sample stream (not shown).

FIG. 3 depicts an exploded diametric view of the compression means 122. In this example of the embodiment the microfluidic liquid junction structure 102 is a round planar element.

Figure 4:
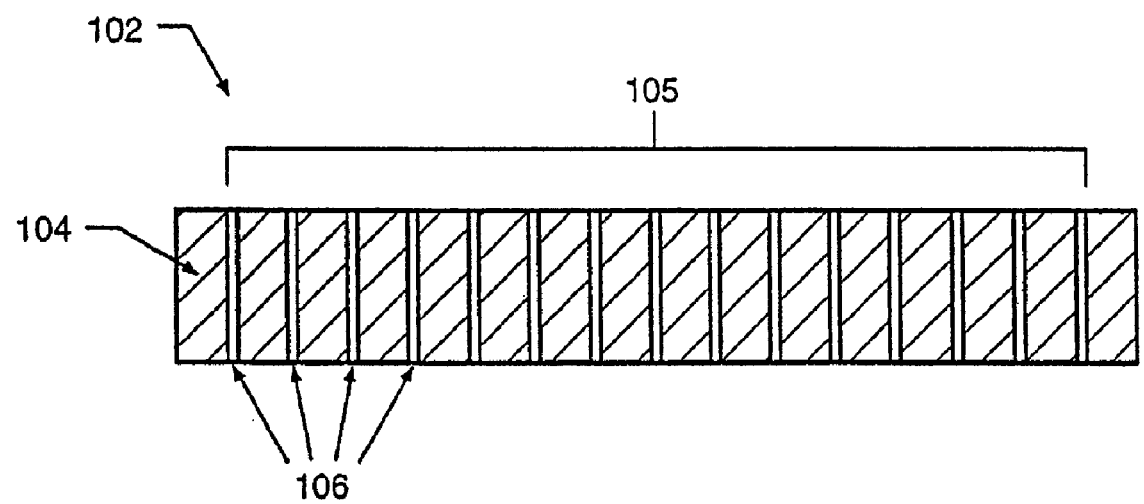
FIG. 4 depicts a schematic cross-sectional view of certain elements of a preferred microfluidic flowing liquid junction structure and a preferred nanochannel array.

FIG. 4 depicts a schematic cross-section of the microfluidic liquid junction structure 102 in its most elementary form, a single planar element. As shown, the microfluidic liquid junction structure 102 is fabricated in a planar substrate 104. Suitable substrate materials are generally selected based upon cost, ease of fabrication, dimensional stability, mechanical strength, and compatibility with the conditions present in the particular environment that the structure will be operating in. Such conditions can include extremes of pH, temperature, ionic concentration, and presence of organic solvents. Useful substrate materials include glass, quartz, ceramic, silicon, polysilicon, as well as polymeric materials such as polycarbonate, polyamide, and other plastics typically utilized in microfabrication techniques.

The junction structure 102 includes a multitude of nanochannels 106 fabricated through the substrate 104 and generally perpendicular to the planar axis of the substrate 104. These nanochannels typically have very small cross-section dimensions, preferably in the range from about 1 nm to 500 nm. It is this small, nanometer scale, cross-sectional width of the nanochannels 106 that gives them their name. For the particular preferred embodiments, nanochannels 106 that have cross section widths of about 10 nm to about 500 nm, and more preferable between about 200 nm and about 300 nm, and lengths of about 0.5 µm to about 200, about 300, and as great as 500 µm will work most effectively, although deviations from these dimensions are within the scope of the invention.

The multitude of nanochannels 106 present in the microfluidic liquid junction structure 102 are referred to collectively as the junction array 105. The size of the array 105 is characterized by the number of nanochannels 106 present in the structure 102. The number of nanochannels can vary from 10 to 100,000,000. More generally, the number of nanochannels can be selected from any whole number less than $10^9$, and can be as low as desired, provided that the effects of the plugging of one or more channel will not substantially and adversely effect the performance of the microfluidic flowing liquid junction. For these particular embodiments discussed below, a junction array 105 with a number of nanochannels 106 between 10 and 100,000 will work most effectively, though deviations from these numbers are within the scope of the invention, as noted above.

The array 105 of nanochannels 106 is a common element in all depicted embodiments of the invention and the operational characteristics of a particular array may be predicted by specifying only three parameters of the array 105: (1) the cross-sectional width of the nanochannel 106, (2) the length of the nanochannel 106, (3) and the number of nanochannels 106 present in the array 105. Table 1 provides ranges expressed in approximate values preferred ranges, for these three parameters.

TABLE 1

Representative Approximate Ranges for Nanochannel Array Parameters

Individual Nanochannel 106 Cross-sectional Width

Range: 1 nm to 900 nm
Preferable ranges: 10 nm to 500 nm; 40 nm to 100 nm; 70 nm
Individual Nanochannel 106 Length Range: 0.5 µm to 900 µm
Preferable ranges: 5 µm to 500 µm; 5 to 20 µm (polymer junction); 100 to 500 µm (glass junction)
Number of Individual Nanochannels 106 in Array 105

Range: 10 to 100,000,000
Preferable ranges: 100 to 1,000,000; 250 to 5,000; 500 to 1,000

Manufacturing of the array 105 of nanochannels 106 and other micro- and nano-scale elements and features into the substrate 104 may be carried out by any number of microfabrication techniques that are well known in the art. For example, photolithographic techniques may be employed in fabricating glass, quartz, ceramic, silicone, polysilicon, or "plastic" polymeric substrates with methods well known in the semiconductor manufacturing industries. Photolithographic masking, plasma or wet etching and other semiconductor processing technologies define microscale and nanoscale elements in and through the substrate and on the substrate's surfaces. Alternatively, micromachining methods, such as laser drilling, micromilling, microgrinding, and the like may be employed. Similarly, for polymeric substrates, such as plastics, well known manufacturing techniques may be used. These techniques include charged particle bombardment and subsequent wet etching of nanoscale and microscale channels through polymeric substrates. Additional techniques include injection molding techniques or stamp molding methods where large numbers of substrates may be produced or polymer microcasting techniques where substrates with microscale and nanoscale features are polymerized within a microfabricated mold.

The microfluidic liquid junction structure 102 may be one planar element or a laminate of multiple planar elements. The planar elements may be attached to each other by a variety of means, including thermal bonding, adhesives, or in the case of glass and some plastics, direct fusion by heating to the melting point. The additional planar elements may constitute all or part of the array structure, or a rigid support element for the array structure element, or such additional layers may include other microfluidic components that integrate into the microfluidic liquid junction structure to provide increased performance or additional features. Such additional elements might include micro scale sensors and sensing elements that measure parameters such as pressure, flow rate, temperature, electrical resistance, oxidation-reduction (redox) potential, conductivity, and pH. These sensors could be utilized to provide feedback concerning the performance of the potentiometric reference electrode 100 and the microfluidic liquid junction structure 102. Such feedback could be utilized by monitor instrumentation for preventative diagnostics of the reference electrode's 100 performance. Such diagnostics might include determining the need for recalibration and predicting and signaling the need for service well before the reference electrode 100 fails in an on-line industrial application.

Figure 5:
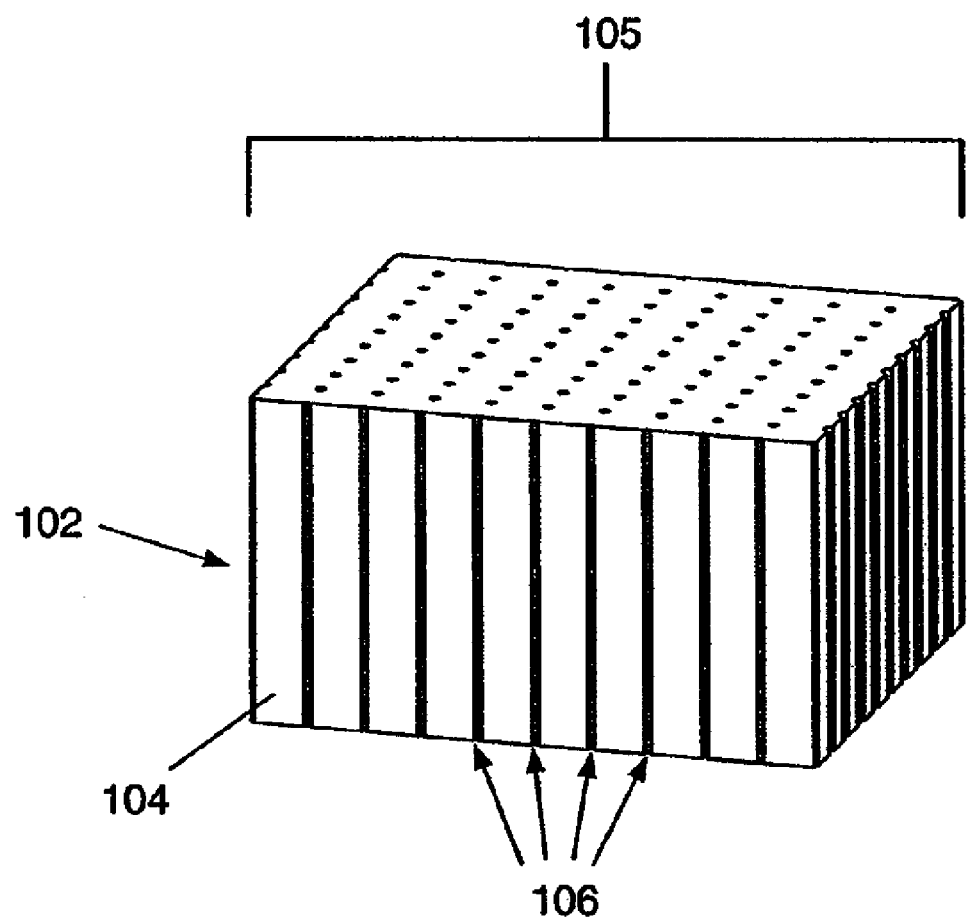
FIG. 5 is an illustrative view representing a single planar polymer microfluidic flowing liquid junction structure in which anisotropic nanochannels have been fabricated.

FIG. 5 depicts an illustrative diametric cross-sectional view of the array 105 of a microfluidic liquid junction structure 102 that is fabricated as a single planar polymer element. The planar element has a specific density (channels/cm$^2$) of etched anisotropic nanochannels 105. In this embodiment of the present invention specific channel densities of generally anisotropic nanochannels were fabricated in 10 µm thick sheets of polycarbonate.

The first step in the fabrication process was to expose 10 µm thick sheets of polycarbonate to charged particles, mostly heavy ions, in a nuclear reactor. These charged particles perforate the polymer sheets and leave "sensitized tracks" in the polymer which are substantially anisotropic. By controlling the duration of the exposure to the charged particles, the density of tracks per square centimeter can be controlled to a high degree of reproducibility. These tracks were generally uniform in width and straight, or anisotropic, and transverse the polymer sheet in a direction generally 90° to the planar axis of the polymer sheet. The tracks in the polymer substrate were preferably etched. This enabled the nanochannels to be selectively etched to channel diameters of 10 nm and larger. The etching process consisted of immersing the polycarbonate sheets in a strong alkaline solution of 6 M NaOH with 10% methanol by volume. To obtain sheets with different channel cross-sectional widths the etch times were varied from 1 hour to 1 minute.

In a final step in the fabrication process, the polycarbonate sheets were coated by dipping them into a bath of 0.5% polyvinylpyrrolidone (PVP) solution. The PVP coating is hydrophilic and it enhances the "wetability" of the polycarbonate sheets and nanochannels.

By design of the nanochannel array 105 density, a flowing microfluidic liquid junction structure 102 was fabricated such that it had the desired number of flowing nanochannels 106 exposed to aperture 130 on one side of the microfluidic flowing liquid junction structure 102, and the corresponding number of flowing nanochannels 106 exposed to orifice 132 on the other side of the microfluidic flowing liquid junction structure 102.

FIG. 6 depicts steps in the fabrication of a flowing microfluidic liquid junction structure 164 from multiple polymer, polyamide planar elements 160 and 162 that may be thermal bonded together into one structure. The two polyamide planar elements can be bonded together using various techniques including those of U.S. Pat. No. 5,525,405 (Coverdall et al.) and U.S. Pat. No. 5,932,799 (Moles).

Anisotropic nanochannels may be fabricated into the polymer polyamide planar element 162 in the same manner as with the polycarbonate planar element previously described above. The polyamide planar element 162 is fabricated to have a specific density of anisotropic nanochannels. The thicker planar element 160 may also be fabricated from polyamide into a honeycomb structure containing relatively larger, micron scale, microchannels 166 with cross-sectional widths on the order of 5 µm to 25 µm in this embodiment. This honeycomb structure of the polyamide planar element 160 adds mechanical strength to the finished microfluidic flowing liquid junction structure 164 without unduly impeding the force of the pressurized electrolyte through the nanochannels 106. The polyamide planar element can be fabricated into a micron scale honeycomb structure by well known photolithography and wet etch techniques such as those reported in U.S. Pat. No. 5,807,406 (Brauker et al.). Due to the relatively regular geometry of the resultant structure the resultant number of active flowing nanochannels 106 may be calculated as the number of nanochannels 106 that face a microchannel 166.

Figure 7:
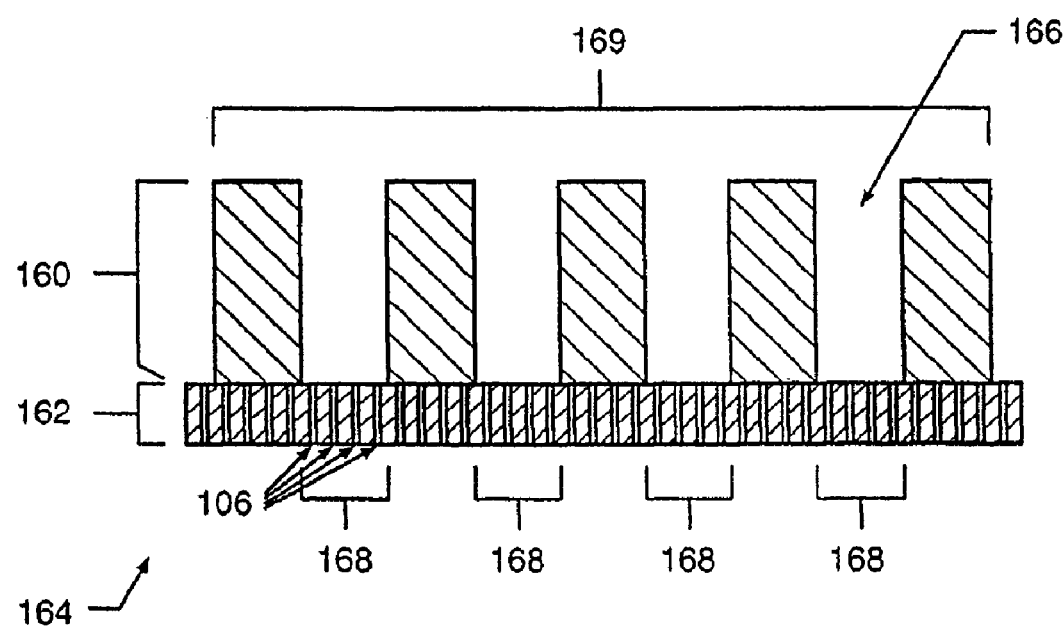
FIG. 7 depicts a detailed schematic cross-section view showing detail of the region in which the nanochannels meet a microchannel in a preferred polymer structure.

FIG. 7 depicts a schematic cross-section of the resultant flowing microfluidic liquid junction structure 164 that is made from two polyamide planar elements, 160 and 162, that have been thermal bonded into one structural element. On the average, each of the microchannels 166 is connected to a small array 168 with approximately the same number of nanochannels 106. In operation, pressurized electrolyte 110 enters into an array 169 of microchannels 166 and exits through the many connected nanochannels 106. In this way pressurized electrolyte 110 flows through an array 169 of many smaller arrays 168 of nanochannels 106. This is a useful technique to build up relatively thick planar structures that do not unduly impede the pressurized flow of electrolyte into the nanochannels 106.

In an alternative embodiment of the invention, additional planar elements of the same or different materials can be bonded on top of the microfluidic flowing liquid junction structure 164 for additional features and performance such as additional strengthening structures, valves, or sensing elements. Such fabrication techniques are well known and are reviewed by Marc Madou in "Fundamentals of Microfabrication", 1997, CRC Press. Referring to FIG. 1, it can be seen that this microfluidic flowing liquid junction structure 164 can be sealed into the exemplary reference electrode 100 by compression means 122. By proper selection of the nanochannel density of planar element 162 and the microchannel density of planar element 160, a microfluidic flowing liquid junction structure 164 can be fabricated such that it has an microchannel array 169 with the desire number of flowing microchannels 166 exposed to aperture 130 and the corresponding, connecting nanochannel arrays 168 with the desired number of flowing nanochannels 106 exposed to orifice 132.

Figure 8:
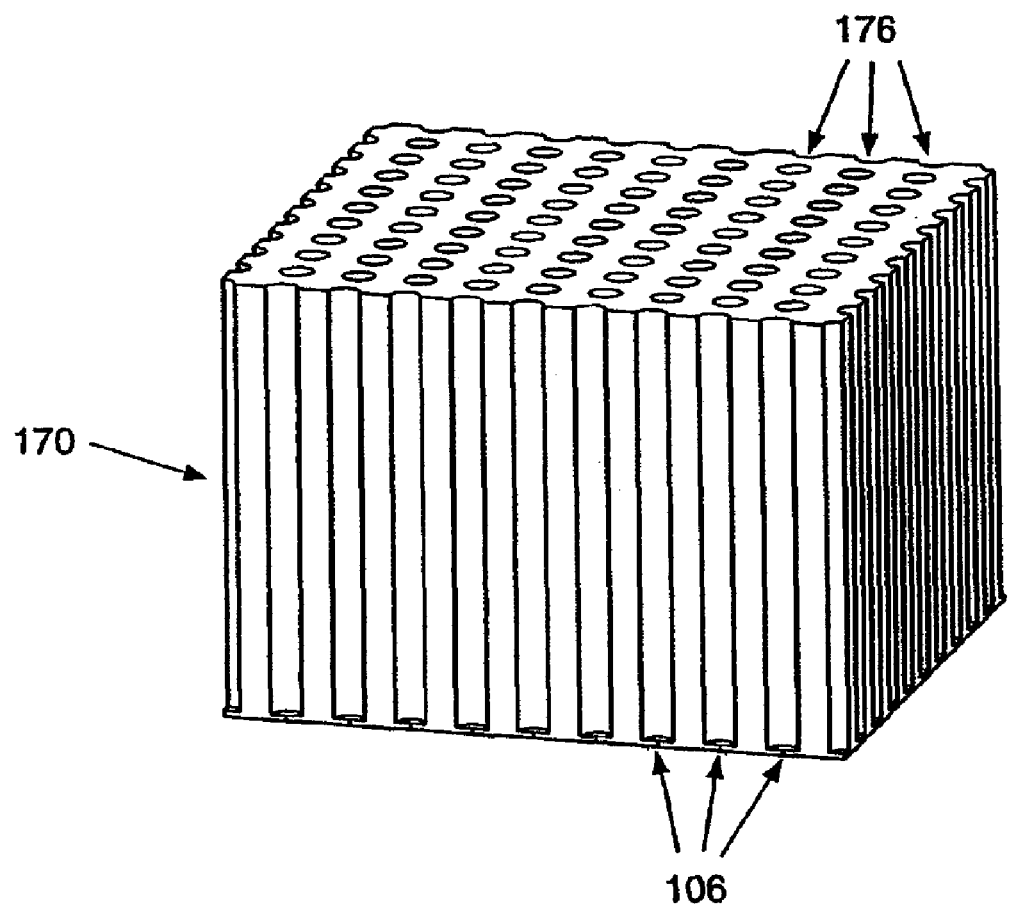
FIG. 8 depicts a diametric illustrative view of a microfluidic flowing liquid junction structure having nanochannels and supporting microchannels that has been fabricated from one planar element of silicon.

FIG. 8 depicts a flowing microfluidic liquid junction structure 170 that can be fabricated from a single planar element of silicon by means of anisotropic plasma etching techniques such as those reported in U.S. Pat. No. 5,501,893 (Laermer et al.). The microfluidic flowing liquid junction structure 170 has micron scale microchannels 176 etched in one side of the structure and connecting nanochannels 106 etched through the other side of the structure.

Figure 9:
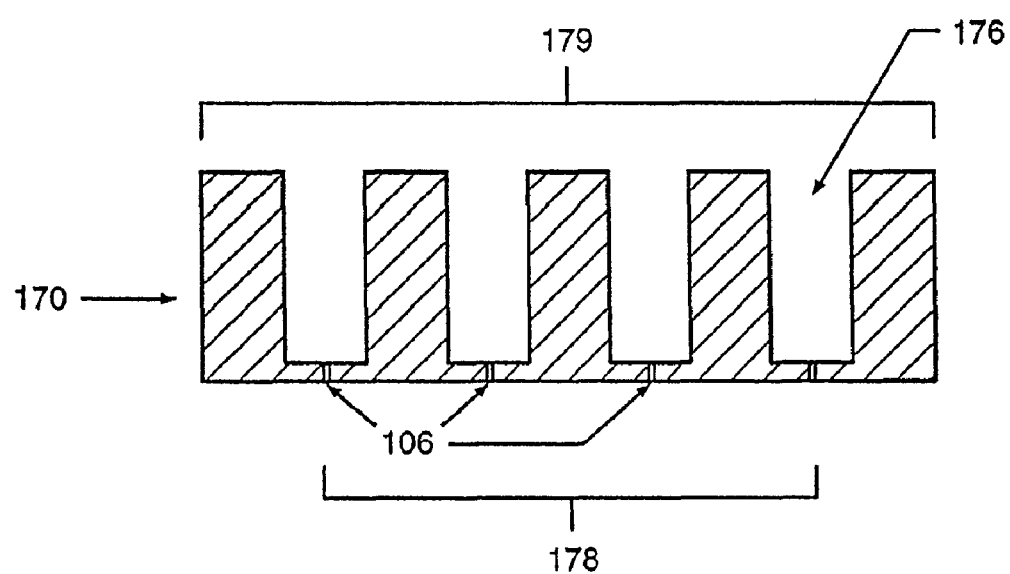
FIG. 9 depicts a schematic cross-section view showing the detail of where the nanochannel meets a microchannel in a silicon microfluidic flowing liquid junction structure.

FIG. 9 depicts a schematic cross-section of the silicon microfluidic flowing liquid junction structure 170. The flowing microfluidic liquid junction structure 170 has an array 179 of microchannels 176 on one side of the structure that connect to an array 178 of nanochannels 106 on the other side of the structure. In this exemplary embodiment the ratio of nanochannels 106 that connect to each microchannel 176 is one to one. Anisotropic plasma etching can fabricate high aspect ratio features in silicon with ratios as high as 20:1. Accordingly, in this embodiment the microchannels 176 can be etched 5 μm wide and 75 μm deep from one side of the structure and the nanochannels 106 can be etched 100 nm wide and up to 2 μm deep from the other side of the microfluidic flowing liquid junction structure 170.

Again, the nanochannel array 178 density and the microchannel array 179 density may be selected such that, a microfluidic flowing liquid junction structure 170 may be fabricated such that it has a microchannel array 179 with the desired number of flowing microchannels 176 exposed to aperture 130 and the corresponding, connected nanochannel array 178 with the desired number of flowing nanochannels 106 exposed to orifice 132. Such a junction may be designed to exhibit certain characteristics suitable to any use.

Figure 10:
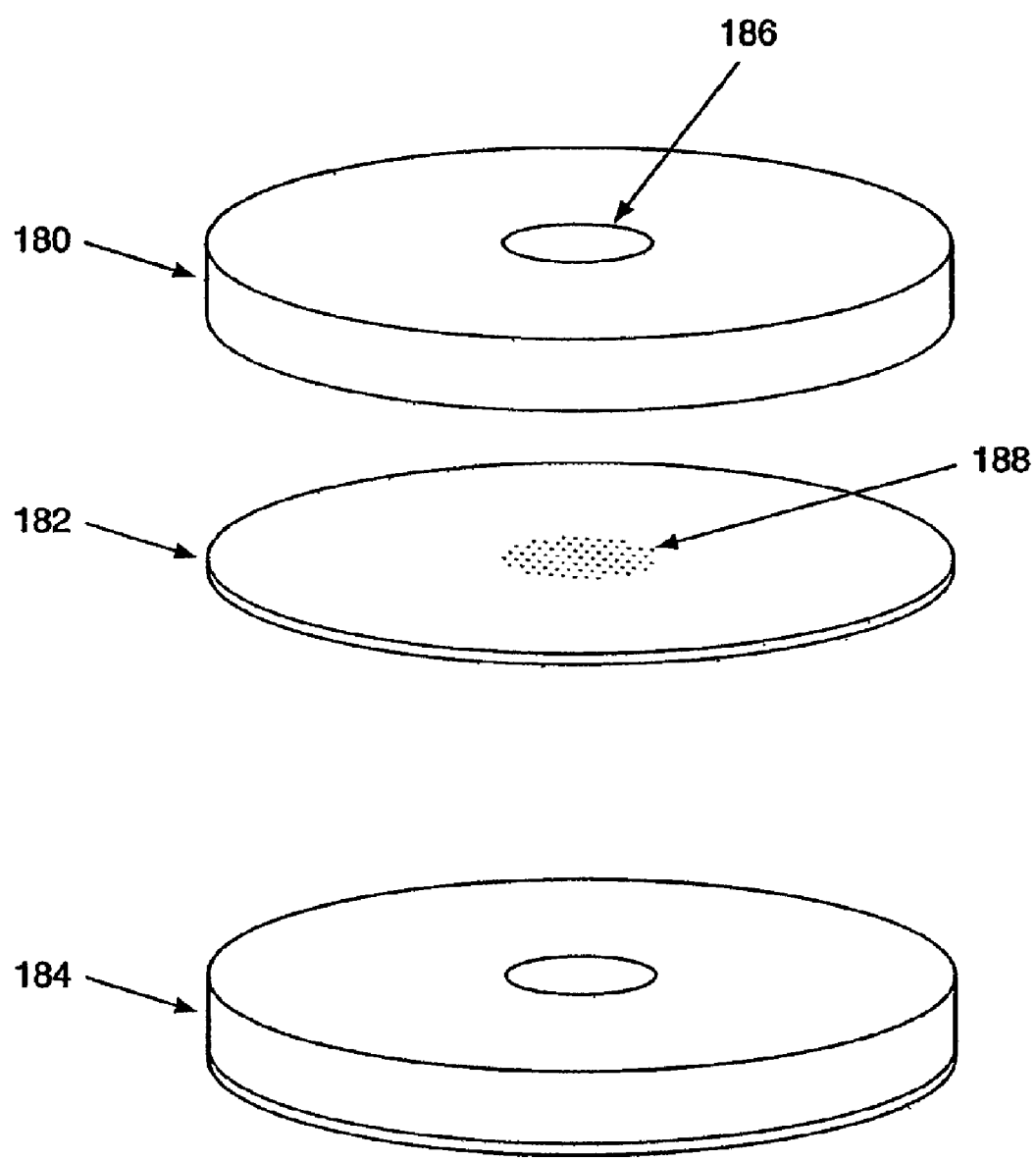
FIG. 10 depicts diametric views illustrating steps in the fabrication of a preferred glass microfluidic flowing liquid junction structure from multiple planar glass elements.

FIG. 10 depicts steps in the fabrication of a flowing microfluidic liquid junction structure 184 from multiple glass planar elements 180 and 182 that can be thermal bonded or fused together into one planar structure. Planar element 180 is a solid element of glass, such as Corning 0120 glass or Corning 8161 glass, that has a single, relatively large channel 186 in the center. The channel 186 can be several microns to 1 mm in diameter and it can be fabricated with well known microfabrication techniques. The planar element 182 is a glass disk that has at its center an array 188 region of nanochannels. This planar element 182 can be made by methods reported in U.S. Pat. No. 5,264,722 (Tonucci et al.) for the manufacture of nanochannel glass rod. Nanochannel glass rod made by this method is essentially a fused bundle of anisotropic glass tubes that each have a cross-sectional width of just a few nanometer to several hundred nanometers. Furthermore, the nanochannel glass rod, which may also be preferably fabricated from Corning 0120 glass or Corning 8161 glass or other suitable glass, can be clad in non-porous glass so that just the core of the resultant glass rod is made up of an array 188 of nanochannels. A single planar cross section 182 of this rod can be cut to use as the nanochannel array 188 of the present embodiment of the present invention. The width of the nanochannels and the number of nanochannels can be precisely controlled by the fabrication methods reported in U.S. Pat. No. 5,264,722 (Tonucci et al.). The length of the nanochannels in the array 188 length can be controlled by cutting a cross-section of the rod and grinding it to the desired thickness.

Where both glass planar layers, 180 and 182, are made from the same glass, they may be fused together into a single flowing microfluidic liquid junction structure 184 by scientific glass blowing techniques well known to those skilled in the art. Alternatively, they may be thermally bonded by the techniques disclosed and reviewed by Marc Madou in "Fundamentals of Microfabrication", 1997, CRC Press.

Figure 11:
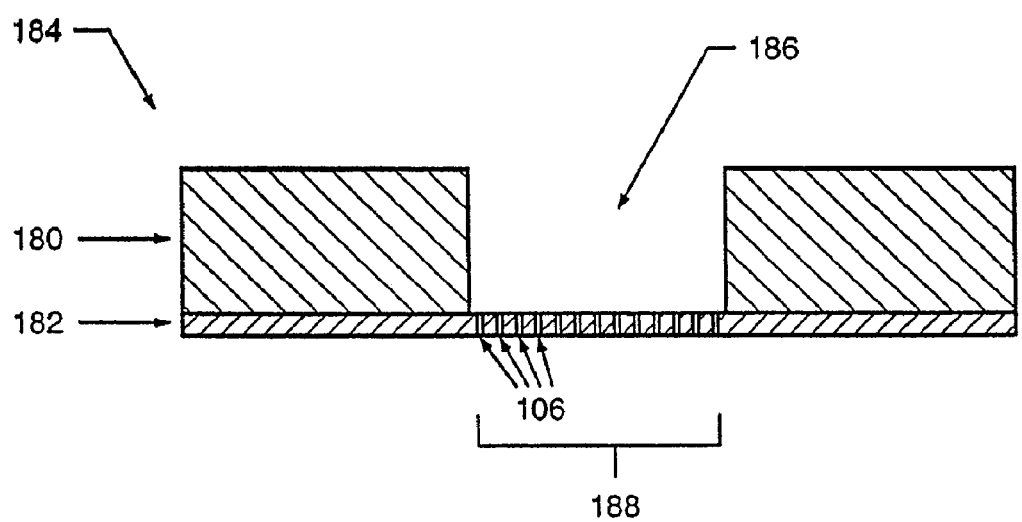
FIG. 11 depicts a schematic cross-sectional view of a glass microfluidic flowing liquid junction structure.

FIG. 11 depicts a schematic cross-section view of the glass flowing microfluidic liquid junction structure 184. The flowing microfluidic liquid junction structure 184 has a single large channel 186 on one side and a corresponding, connecting array 188 of nanochannels 106 on the other side. The planar element 180 lends mechanical strength to the planar element 181 in this embodiment of the present invention once they are bonded or fused together into the single planar flowing microfluidic liquid junction structure 184.

As before, by design of the nanochannel array 188 density and the size of the single channel 186, a microfluidic flowing liquid junction structure 184 may be fabricated such that the single channel 186 aligns with the aperture 130 and the corresponding, connected nanochannel array 188 with the desired number of flowing nanochannels 106 are exposed to orifice 132.

TABLE 2

Representative Operational Specifications
of Flowing Microfluidic Liquid Junctions Electrolyte Linear Velocity Range: >1 μm/sec
Preferable Range: greater than approximately 0.1 cm/sec
Most Preferable range: greater than approximately 1.0 cm/sec
Electrolyte Volumetric Flow Rate Range: less than approximately 1500 μl/day (about 500 ml/yr)
less than approximately 60 μl/hr
Preferable range: less than approximately 150 μl/day (about 50 ml/yr)
less than approximately 6 μl/hr
Electrical Resistance Range: less than approximately 100 MO
Preferable range: less than approximately 1 MO Experimental and Theoretical Data Based Upon Experimental Data Tables 3 and 4, presented below, detail certain actual physical and potentiometric characteristics, and estimated physical and potentiometric characteristics based upon and extrapolated from the actual physical and potentiometric characteristics, of microfluidic flowing liquid junctions of the invention having various structural characteristics.

Table 3 provides experimental test data for reference electrodes having exemplary flowing microfluidic liquid junction structures within the scope of the present invention. Transient, static and stirring errors were determined in standard pH 7 buffer solutions after consecutive exposures to the test solution. The potential was measured against a pH-sensitive glass electrode. The exemplary microfluidic flowing liquid junction structure material was obtained from Osmonics Laboratory Products (Westborough, Mass., USA). The Osmonics part number for the 30 nm nanochannel microfluidic flowing liquid junction material, P/N KN3CP01300; the Osmonics part number for the 50 nm nanochannel microfluidic flowing liquid junction material, P/N KNSCP01300. The BJC Model 9015, P/N C2451C-12A, with typical commercially available diffusion junction reference electrode was obtained from Broadley-James Corp. (Irvine, Calif., USA).

TABLE 3

Microfluidic Flowing Liquid Junction Reference Electrode Tests
Comparative Reference Electrode Tests: Microfluidic Flowing Liquid Junctions vs. Conventional Non-Flowing Diffusion Junction

| Test Solution | Reference Electrode | Channel Width | Channel Length | Array Size | Pressure | Flow Rate (µl/hr) | Velocity (cm/s) | Transient Error (mV) | | Static Error (mV) | | Stirring Error (mV) | |
|---|---|---|---|---|---|---|---|---|---|---|---|---|---|
| pH 4 Buffer | MLJ Design | 50 nm | 6 µm | 1,000,000 | 40 psig | 1910 | 6.4 | 0.2 | <0.1 | −0.2 | 0.1 | <0.1 | <0.1 |
| | MLJ Design | 30 nm | 6 µm | 1,000,000 | 40 psig | 70 | 0.7 | 0.3 | <0.1 | <0.1 | <0.1 | <0.1 | <0.1 |
| | MLJ Design | 50 nm | 6 µm | 1,000,000 | 10 psig | — | — | 0.1 | <0.1 | 0.1 | <0.1 | <0.1 | <0.1 |
| | MLJ Design | 30 nm | 6 µm | 1,000,000 | 10 psig | — | — | 0.2 | <0.1 | 0.1 | <0.1 | <0.1 | <0.1 |
| | MLJ Design | 70 nm | 10 µm | 1000 | 40 psig | 1.8 | 13 | 0.1 | 0.2 | 0.1 | <0.1 | 0.3 | 0.4 |
| | BJC Model 9015 | gel electrolyte with non-flowing diffusion junction | | | N/A | N/A | N/A | 1.5 | 0.6 | −2.6 | −2.9 | 1.3 | 0.9 |
| 0.1 M HCl | MLJ Design | 50 nm | 6 µm | 1,000,000 | 40 psig | 741 | 2.5 | <0.1 | <0.1 | <0.1 | <0.1 | 0.1 | 0.2 |
| | MLJ Design | 30 nm | 6 µm | 1,000,000 | 40 psig | 193 | 1.8 | <0.1 | <0.1 | <0.1 | <0.1 | 0.2 | 0.3 |
| | MLJ Design | 50 nm | 6 µm | 1,000,000 | 10 psig | 114 | 0.4 | <0.1 | <0.1 | <0.1 | <0.1 | <0.1 | 0.1 |
| | MLJ Design | 30 nm | 6 µm | 1,000,000 | 10 psig | 20.3 | 0.2 | <0.1 | <0.1 | <0.1 | <0.1 | 0.1 | 0.1 |
| | BJC Model 9015 | gel electrolyte with non-flowing diffusion junction | | | N/A | N/A | N/A | 5.2 | −4.1 | −2.3 | 2.2 | 0.6 | 1.7 |
| 0.1 mM HCl | MLJ Design | 50 nm | 6 µm | 1,000,000 | 40 psig | 583 | 2.0 | <0.1 | <0.1 | <0.1 | 0.2 | <0.1 | 0.2 |
| | MLJ Design | 30 nm | 6 µm | 1,000,000 | 40 psig | 20 | 0.19 | <0.1 | 0.2 | <0.1 | 0.3 | 0.9 | 1.2 |
| | MLJ Design | 50 nm | 6 µm | 1,000,000 | 10 psig | 95 | 0.32 | 0.1 | 0.3 | <0.1 | <0.1 | 0.1 | 0.4 |
| | MLJ Design | 30 nm | 6 µm | 1,000,000 | 10 psig | 47 | 0.44 | 0.1 | 0.2 | <0.1 | <0.1 | 0.1 | 0.2 |
| | BJC Model 9015 | gel electrolyte with non-flowing diffusion junction | | | N/A | N/A | N/A | −3.2 | 22.5 | −2.7 | 1.4 | 10.5 | 12 |
| 1 M Tris Buffer | MLJ Design | 50 nm | 6 µm | 1,000,000 | 10 psig | 374 | 1.3 | −0.2 | −0.2 | 1.4 | −0.9 | −0.2 | 0.1 |
| | MLJ Design | 30 nm | 6 µm | 1,000,000 | 10 psig | 39 | 0.4 | 0.9 | 1.1 | −0.2 | 1.8 | 0.3 | 0.2 |
| | BJC Model 9015 | gel electrolyte with non-flowing diffusion junction | | | N/A | N/A | N/A | 24 | 26 | −4.5 | −1.9 | 1.6 | 0.8 |

Table 4 provides the estimated resistance, velocity and lifetime of exemplary microfluidic flowing liquid junction structures within the scope of the present invention. Table 4 was generated based on the actual, experimentally determined data derived from a microfluidic flowing liquid junction structure with 1,000 10-µm long, nanochannels having widths of approximately 70 nm (see bottom row), specially prepared as described herein.

TABLE 4

ELECTRODE CHARACTERISTICS/THEORETICAL
LIFETIME ESTIMATES FOR VARIOUS JUNCTION DESIGNS
Electrode Lifetime Estimates for Selected MLJ Designs
(Derived from Junction Linear Flow and Resistance Data)

| Channel Dimensions | | Array Size | Estimated Total Resistance | Est. Linear Velocity | Est. Lifetime (yrs) for 50 ml |
|---|---|---|---|---|---|
| ID (nm) | Length (µm) | (# of Channels) | (kΩ) | (cm/s) (40 psig) | of Electrolyte |
| 10 | 6 | 1,000 | 1,910.83 | 0.44 | 4568.11 |
| 10 | 6 | 10,000 | 191.08 | 0.44 | 456.81 |
| 10 | 6 | 100,000 | 19.11 | 0.44 | 45.68 |
| 10 | 6 | 1,000,000 | 1.91 | 0.44 | 45.7 |
| 30 | 6 | 1,000 | 212.31 | 3.98 | 56.40 |
| 30 | 6 | 10,000 | 21.23 | 3.98 | 5.64 |
| 30 | 6 | 100,000 | 2.12 | 3.98 | 0.56 |
| 30 | 6 | 1,000,000 | 0.21 | 3.98 | 0.06 |
| 50 | 6 | 1,000 | 76.43 | 11.05 | 7.31 |
| 50 | 6 | 10,000 | 7.64 | 11.05 | 0.73 |
| 50 | 6 | 100,000 | 0.76 | 11.05 | 0.07 |
| 50 | 6 | 1,000,000 | 0.08 | 11.05 | 0.01 |
| 70 | 10 | 1,000 | 64.99 | 13.00 | 3.17 |

Filtration-Enhanced Reference Electrode

Figure 14:
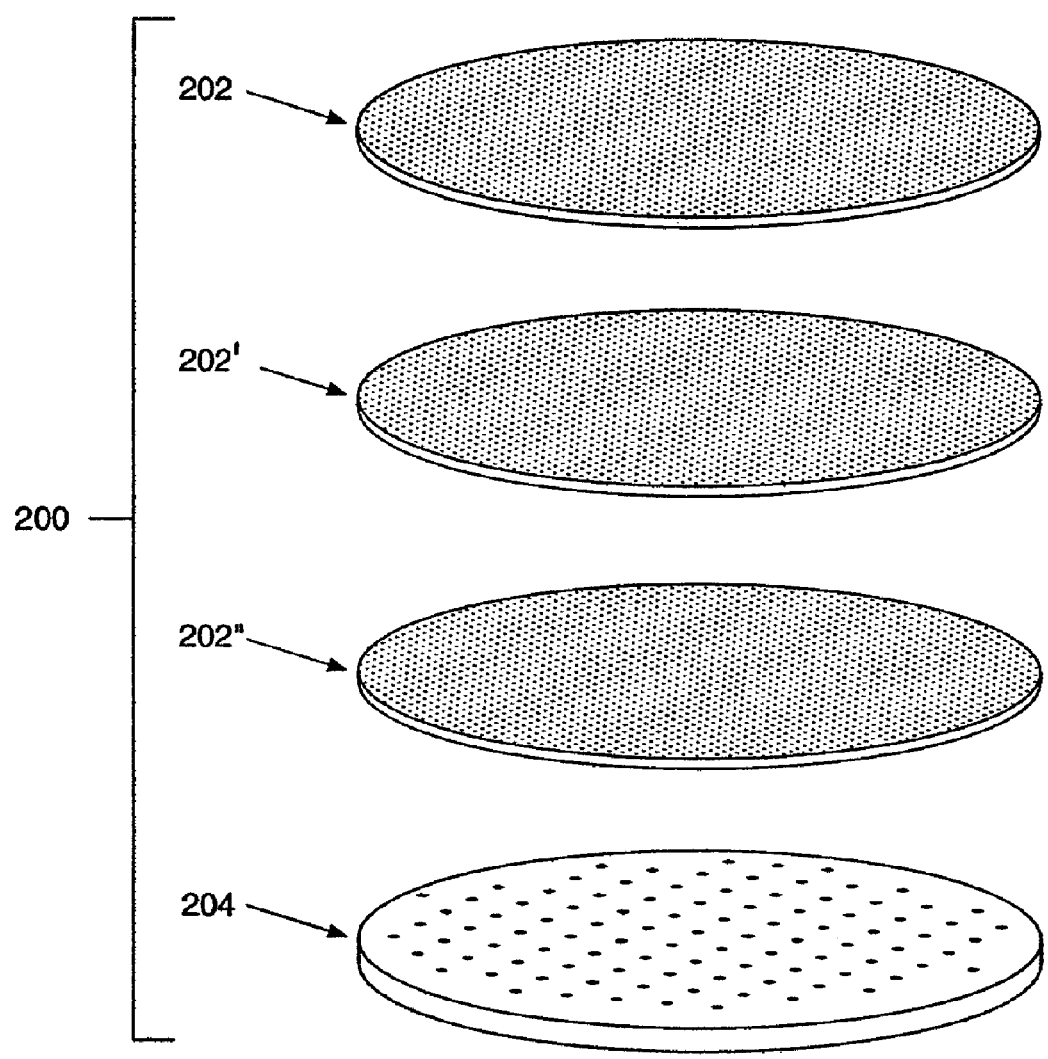
FIG. 14 is a schematic perspective view of a system having multiple filters in conjunction with a microfluidic flowing liquid junction.

One aspect of the junction disclosed herein concerns a reference electrode having an internal, electrolyte filtration mechanism configured to work in conjunction with a microfluidic flowing liquid junction. The resulting structure is designed to, optionally, substantially enhance the longevity and stability of the microfluidic flowing liquid junction, yielding an enhanced junction assembly. FIG. 14 shows a schematic exploded perspective view of such an enhanced microfluidic flowing liquid junction 204 configured to work in combination with one or more filtration members 202, 202', and 202". The microfluidic flowing liquid junction 204 may be, for example, any embodiment of a microfluidic flowing liquid junction as has been described above. For convenience, the structure resulting from combining the microfluidic flowing liquid junction with one or more filtration members 202, 202', 202", etc., is referred to here as a filtration-enhanced microfluidic flowing liquid junction 200.

The inner diameter of each nanochannel in the liquid junction structure 204 is preferably within the range of 50 nm to 500 nm, including 100, 200, 300 and 400 nm. The length of the nanochannels in the junction is preferably substantially uniform and within the range of 5 μm to 500 μm, including 10, 20, 50, 100, 200, 300 and 400 μm. The number of nanochannels in the liquid junction structure is preferably from 10 to 10,000,000, including 100, 1000, $10^5$, and $10^6$. In some embodiments of the invention, the nanochannels of the liquid junction structure are preferably substantially clustered inside a 1 mm$^2$ area on the array substrate.

The junction assembly 200 allows for a sustained and prolonged flow of electrolyte through the microfluidic flowing liquid junction's array of nanochannels by passing the electrolyte from the electrolyte reservoir 110 (see FIG. 1) through one or more high flux, high capacity filters 202, 202', 202". The high flux, high capacity filters 202, 202', and 202" each contains pores having inside diameters that are about the same or smaller in size than the inside diameters of the nanochannels of the liquid junction structure 204. Such filters may be isotropic or anisotropic and may be manufactured out of any of a variety of materials, including but not limited to glass, polycarbonate, silicon and/or ceramic. The pores of the filtration members 202, 202', and 202" are preferably configured to substantially remove, from the electrolyte solution that passes through the filtration members 202, 202', and 202", particles that are large enough to clog nanochannels of the nanochannel array of the liquid junction structure 204. In this manner, the filters 202, 202', and 202" forestall clogging of the nanochannels of the nanochannel array of the liquid junction structure 204.

As will be detailed below, the filters 202, 202' and 202" contain pores or pore networks in a quantity such that each of these filtration members has the capacity to allow a flow rate of electrolyte that substantially exceeds the flow rate capacity of the liquid junction structure 204. It is preferred that the microfluidic flowing liquid junction 204, rather than the filters 202, 202', or 202", singly or in combination, be the component that determines or limits the linear flow rate of the electrolyte through the junction assembly 200. As already explained, one aspect of the invention is directed to ensuring that the electrolyte flows at a linear velocity sufficient to substantially eliminate back diffusion of the sample solution into the liquid junction structure 204.

In one embodiment of the enhanced junction assembly 200, the ratio of electrolyte flux capacity through each of the filters 202, 202', and 202" to the electrolyte flux capacity through the nanochannel array is configured to be sufficiently high. This ensures that as a percentage of the pores of the filter 202 (or 202' or 202") trap particulates and become clogged over time, there remains sufficient capacity in the filter 202 to permit the passing of sufficient filtered electrolyte to the nanochannel array so that the desired electrolyte velocity through the nanochannel array is achieved and maintained. Furthermore, the filtering capacity of a filter 202, 202', or 202" may be configured to be sufficiently greater than that of the liquid junction structure 204 so that electrolyte flows through the liquid junction structure 204 at a substantially constant velocity for days, weeks, months, years, or even decades on a small amount of electrolyte.

Another aspect of the enhanced junction assembly concerns a reference electrode that uses an internal filtration system working in conjunction with a microfluidic flowing liquid junction to produce sustained and prolonged flow of electrolyte through a nanochannel array of the microfluidic flowing liquid junction 204. The flow of the electrolyte through the nanochannel array of the liquid junction structure 204 has sufficient linear velocity such that sample solution is substantially prevented from back diffusing into the nanochannels of the nanochannel array. At least one high flux, high capacity filter 202 is positioned between the electrolyte reservoir 110 and the microfluidic flowing liquid junction 204.

The filtration members 202, 202', and 202" are selected to substantially prevent or minimize clogging of the nanochannel array by allowing passage only of particles that are small enough to pass cleanly through the nanochannels of the liquid junction structure 204. In addition, the filter 202, for example, is configured to have substantially more pores than the liquid junction structure 204; in this manner, as a percentage of the pores of filter 202 become clogged over time, the filter 202 still allows ample flow of electrolyte to the liquid junction structure 204. In this embodiment, preferably each nanochannel of the liquid junction structure 204 receives enough electrolyte such that the linear velocity of electrolyte is sufficient to substantially prevent back diffusion of the sample solution into the nanochannels of the liquid junction structure 204.

Another feature of the enhanced junction assembly consists of a method for producing a sustained and prolonged flow of electrolyte through nanochannels with inside diameters of less than 500 nanometers using a high flux, high capacity filter to prevent clogging of a microfluidic flowing liquid junction structure with particulate matter that may be present in a reference electrolyte solution.

Another aspect of the enhanced junction concerns a method of filtering the electrolyte 110 prior to passing it through the nanochannel array of the liquid junction structure 204. The method comprises providing at least one filter, for example 202, having a relatively high flux such that the linear velocity of electrolyte through the nanochannel array of the liquid junction structure is substantially unchanged.

Another feature of the enhanced junction provides a method of filtering the electrolyte 110 prior to passing the electrolyte 110 through the liquid junction structure 204 with a filter 202 having sufficient capacity such that even after a substantial percentage of the pores of the filter 202 have clogged with particulate material, the filter 202 allows passage of a sufficient amount of electrolyte 110 to the liquid junction structure 204 in order to ensure that the linear velocity of the electrolyte 110 through each nanochannel is sufficient to prevent back diffusion of the sample solution into the nanochannels.

Another aspect of the invention concerns a pressurized flow of electrolyte 110 through a nanofiltration membrane (e.g., filter 202) and a microfluidic flowing liquid junction (e.g., liquid junction structure 204), wherein the nanofiltration membrane is capable of allowing an electrolyte flux that is much greater than the electrolyte flux of which the microfluidic flowing liquid junction is capable. This ensures that the nanochannel array of the microfluidic flowing liquid junction is the back-pressure determining structure. This allows positioning the filter 202, for example, adjacent to the liquid junction structure and allows the electrolyte 110 to flow through the filter 202 into a discrete layer of electrolyte and then through the liquid junction structure 204. In this way, the filter 202 can be placed spaced either immediately adjacent to or substantially apart from the liquid junction structure 204 without any portion of the filter 202 blocking electrolyte flow into any of the individual nanochannels of the microfluidic flowing liquid junction 204. The electrolyte 110 flows through the pores of the filter 202 and feeds all the nanochannels in the liquid junction structure 204 in sufficient volume such that electrolyte flow through the individual nanochannels of the microfluidic flowing liquid junction 204 has substantially the same flux and linear velocity.

Figure 15:
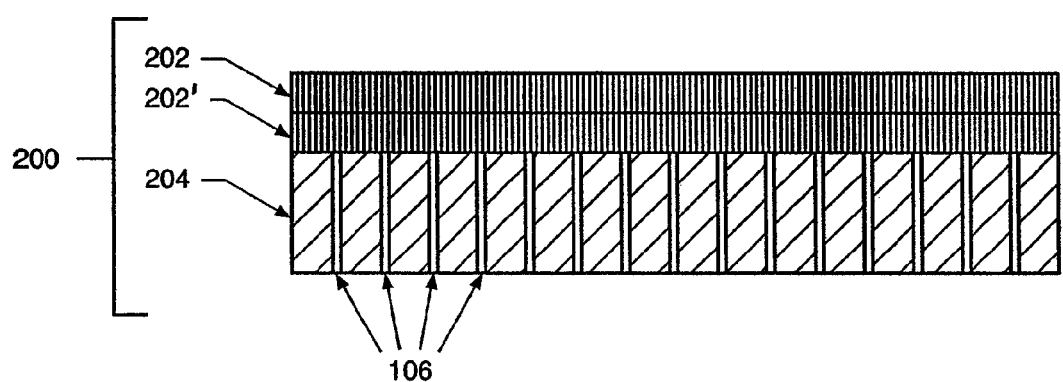
FIG. 15 is a schematic cross-sectional view of one embodiment of a microfluidic flowing liquid junction and multiple filtration members configured to form an enhanced microfluidic flowing liquid junction.

FIG. 15 is a schematic cross-sectional view of one embodiment of a microfluidic flowing liquid junction 204 and multiple filtration members 202 and 202' configured to form an enhanced microfluidic flowing liquid junction 200. FIG. 15 shows en embodiment of the assembly 200 where two filtration members, namely the filters 202 and 202', have been "stacked" on the microfluidic flowing liquid junction 204. The filter 202' is placed immediately adjacent to the microfluidic flowing liquid junction 204, and the filter 202 is placed immediately adjacent to the filter 202'. In this configuration, the filter 202' has at least one pore which has a diameter that is about the same size or smaller than the diameter of the nanochannels 106 of the microfluidic flowing liquid junction 204. Additionally, the filter 200 may have pores with diameters that are larger, the same, or smaller than the diameters of the pores of the filter 200'.

Figure 16:
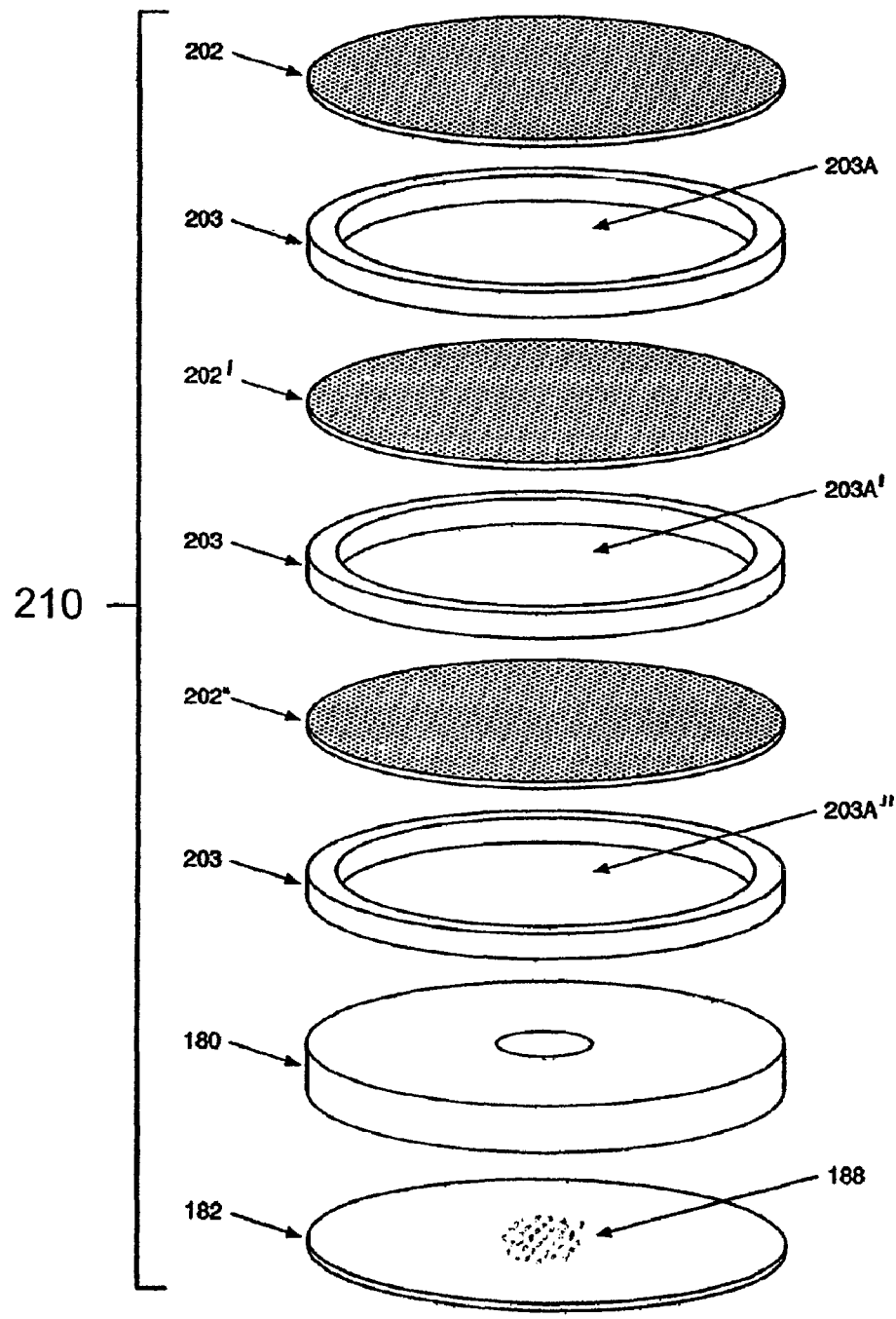
FIG. 16 is a schematic, exploded, perspective view of one embodiment of a filtration-enhanced reference electrode system having a microfluidic flowing liquid junction cooperating with multiple filtration members.

FIG. 16 shows a diagrammatic perspective view of an enhanced junction 210 according to one embodiment of the invention. The enhanced junction 210 comprises at least one filter 202 that is optionally bonded to a support member 203. As shown, in some embodiments, the enhanced junction may have several filtration members 202, 202', and 202" with corresponding support members 203, 203', and 203". The support members 203, 203', and 203" may also functions as spacers between the filtration members 202, 202', and 202" and, in the case shown, between filtration member 202" and the support 180 for the slice of glass 182 having the nanochannel array 188 (See FIG. 10 and accompanying description). In some embodiments, the spacer member 203 provides a space 203A for receiving a layer of electrolyte.

The filtration member 202 may have any shape and may be made of any suitable permeable or semi-permeable material, which may be partly or wholly hydrophobic, partly or wholly hydrophilic, ion selective (either cation or anion selective), isotropic or anisotropic. As noted above, the filtration member 202 may be made of, for example, polycarbonate, glass, polyester, PET, cellulose acetate, cellulose ester, mixed cellulose esters (nitrate and acetate), polyether sulfone (PES), polyvinylidene fluoride (PVDF), polytetrafluoroethylene (PTFE), polypropylene, nylon, polyvinylchloride (PVC), polyamide, or any suitable porous material.

The support member 203 may be made of any polymer material, or any non-water-soluble, inert material. The support member 203 may be comprised of, for example, polycarbonate, glass, polyester, PET, cellulose acetate, cellulose ester, mixed cellulose esters (nitrate and acetate), polyether sulfone (PES), polyvinylidene fluoride (PVDF), polytetrafluoroethylene (PTFE), polypropylene, nylon, polyvinylchloride (PVC), polyamide, or any similar materials. The support member 180 may be, for example, the glass component discussed with reference to FIG. 6 or FIG. 10. Hence, the support member 180 adds mechanical strength to the slice of glass 182 having the nanochannel array 188. The nanochannel array 188 may be any microfluidic flowing liquid junction as has been described above.

Figure 17:
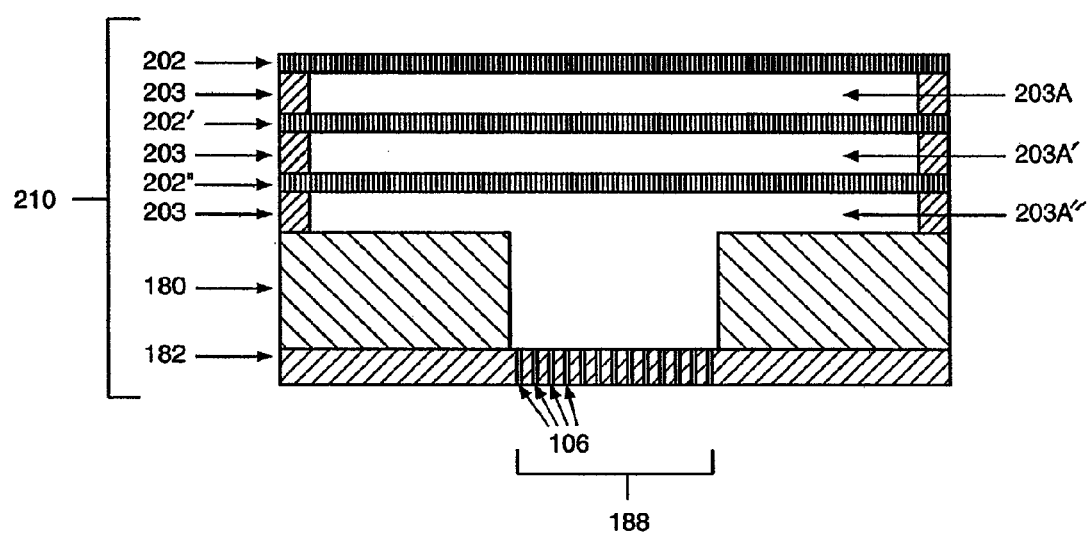
FIG. 17 is a schematic, assembly, cross-sectional view of the microfluidic flowing liquid junction and filtration members of FIG. 16.

FIG. 17 is a schematic, cross-sectional, assembly view of the microfluidic flowing liquid junction and filtration members 202', 202", and 203" described with reference to FIG. 16. In this embodiment, support members 203 and 203' separate the filtration members 202, 202', and 202" from each other, while support member 203" separates filtration member 202" from the support 180. As is shown, the support members 203, 203', and 203" may be configured to provide gaps 203A, 203A', and 203A" for receiving a layer of electrolyte. In other embodiments, however, the assembly 210 may be configured without such gaps. In that case, the support members 203A, 203A', and 203A" may not be incorporated into the assembly 210; rather, the filtration members 202, 202', and 202" are placed directly adjacent to one another. The structures 180 and 182 may be considered an alternative embodiment of the junction structure 204, as shown in both of FIGS. 14 and 15.

In a preferred embodiment of the enhanced junction, the size of the inner diameter of the pores of the filter 202 ($\emptyset_F$) is smaller than the inner diameter of the nanochannels of the liquid junction structure 204 ($\emptyset_J$). For example, $\emptyset_F$ may be 100 nm while $\emptyset_J$ may be 400 nm. In another embodiment, comprising plural filtration members 202 and 202', filtration member 202 has pores with inner diameter of 50 nm, and filtration member 202' has pores with inner diameter of 100 nm, while the liquid junction structure 204 has nanochannels with inner diameter of 400 nm. Alternatively, the inner diameter of the pores of the filters 202 or 202' are substantially the same as the pores of the liquid junction member 204.

Another feature of the enhanced junction assembly 200 is that the number of pores in the filter 202 is greater, and preferably substantially greater, than the number of nanochannels in the liquid junction structure 204. For example, the number of pores in the filter 202 may be $10^6$, while the number of nanochannels in the liquid junction structure 204 may be as low as 10, 100 or 1000.

Another aspect of the enhanced junction assembly is that preferably the volumetric flow capacity of the filter 202 is greater than that of the liquid junction structure 204. This is to ensure that the liquid junction structure 204 is the structure that limits the linear flow rate of the electrolyte exiting the reference electrode. The flow rate capacity of the liquid junction structure 204 is preferably lower than that of any one filtration member 202, 202', or 202", etc.

In some embodiments, the filtration members 202, 202', and 202" are preferably configured such that the flow rate through the filtration members 202, 202', and 202" does not result in a significant pressure drop across the filtration members.

In operation, a reference electrode 100 is configured with an enhanced junction assembly 210 in substantially the same way as shown in FIG. 1, except that the junction structure 102 is replaced with the enhanced junction assembly 210 of FIG. 16. The pressurized electrolyte 110 flows through the filtration member 202 and into the space 203A defined by the support member 203. The filtration member 202 substantially prevents submicron particulates from passing into the space 203A.

Even with the use of cleanroom technologies, it is difficult to produce electrolyte solution that is completely free of particulates that may clog the nanochannels of the liquid junction structure 204. Hence, a filter member, for example 202, may be thought of as performing "internal filtration" which results in cleaner electrolyte solution than can be achieved otherwise. By preventing relatively large particulates from passing into the space 203A, the filtration member 202 prevents these particulates from clogging the relatively smaller nanochannels of the liquid junction structure 188, for example.

Preferably the enhanced junction assembly comprises a space between the filtration member 202 and the liquid junction structure 204 to accommodate a layer of electrolyte. This space need not be large, just sufficient to accommodate a layer of electrolyte.

With reference to FIG. 14, the filter 202 is preferably configured to be a low flow resistance filter. The filter 202 is positioned between the electrolyte reservoir 110 and the microfluidic flowing liquid junction 204. The low resistance filter 202 is positioned upstream from the liquid junction structure 204 and may contain multiple filtration members. The total flow resistance of the filters 202, 202', and 202" is preferably lower than the flow resistance associated with the liquid junction structure 204 to ensure that the rate of electrolyte flow through the liquid junction is limited only by the liquid junction structure 204. Hence, the filters 202, 202', and 202" are most preferably configured such that the pressure drop across these filters is much less than the pressure drop across the entire liquid junction. The filters 202, 202', and 202" provide "internal filtration" of the electrolyte 110 which prevents particulates present in the electrolyte 110 from clogging the nanochannels of the microfluidic flowing liquid junction 204. The inner diameter of the pores the filter 202 adjacent to the junction array 204 is preferably substantially the same as or smaller than the inner diameter of the nanochannels in the liquid junction structure 204.

The filtration member 202 has a plurality of pores that may be of any shape, placed in a regular or irregular pattern, and are preferably substantially evenly distributed throughout the surface area of the filtration member 202. The filtration member 202 may also be of any shape.

Preferred Embodiments

Experimental Results and Theoretical Considerations

Experimental data and theoretical considerations based on experiments using preferred embodiments will now be described with reference to Table 5 below.

In the experiment denominated E-1007, as can be observed, the first filtration member (Filter 1) has pores with an average inner diameter (in this example, 100 nm) that is less than one-half the average inner diameter of the nanochannels of the liquid junction structure (in this example, 231 nm). However, the number of pores in the Filter 1 (in this example, $12.6 \times 10^6$) is much greater than the number of pores in the liquid junction structure (in this example, $12.6 \times 10^3$). Additionally, the length of the nanochannels of the liquid junction structure (in this example, 15 μm) is greater than the length of the pores of the filtration member 1 (in this example, 6 μm). Consequently, the Filter 1 has a low calculated resistance (in this example, 0.0607 kO) that is much smaller than the resistance of the liquid junction structure (in this example, 28.42 kO). This ensures that the Filter 1 is capable of allowing a much greater flux of electrolyte than the liquid junction structure, and consequently, the liquid junction structure is the volumetric flow rate limiting structure. Thus, here, electrolytic resistance serves as an approximation of the reciprocal of the volumetric flow.

Experiments E-1019, E-1022, and E-1023 show similar configurations as that exemplified by E-1007, where the filter, or filters in the case of E-1022, has a resistance that is much smaller than the resistance of its associated liquid junction structure. It will be apparent to the person of ordinary skill in the relevant technology that a low resistance filter may be configured through suitable selection of the number of pores, the inner diameter of the pores, and the pore length.

TABLE 5

| Experiment | Filter 2 | Filter 1 | Junction Structure | Enhanced Junction Assembly |
|---|---|---|---|---|
| E-1007 | | (Osmonics) | (Osmonics) | |
| number of pores | — | $12.6 \times 10^6$ | $12.6 \times 10^3$ | |
| pore inner diameter (nm) | — | 100 | 231 | |
| pore length (μm) | — | 6 | 15 | |
| calculated resistance* (k?) | — | 0.0607 | 28.42 | 28.48 |
| E-1019 | (Whatman) | (Osmonics) | (Osmonics) | |
| number of pores | — | $3.14 \times 10^6$ | $3.14 \times 10^3$ | |
| pore inner diameter (nm) | >20 | 100 | 280 | |
| pore length (μm) | 60 | 6 | 15 | |
| calculated resistance (k?) | <<0.2434* | 0.2434 | 77.62 | 77.86 |
| E-1022 | (Osmonics) | (Osmonics) | (Osmonics) | |
| number of pores | $3.14 \times 10^6$ | $3.14 \times 10^6$ | 628 | |
| pore inner diameter (nm) | 200 | 100 | 175 | |
| pore length (μm) | 6 | 6 | 6 | |
| calculated resistance (k?) | 0.0609 | 0.2434 | 397.4 | 397.7 |
| E-1023 | | (Osmonics) | (Osmonics) | |
| number of pores | — | $3.14 \times 10^6$ | 628 | |
| pore inner diameter (nm) | — | 100 | 175 | |
| pore length (μm) | — | 6 | 6 | |
| calculated resistance (k?) | — | 0.2434 | 397.4 | 397.6 |

*Resistances were calculated assuming a 4M KCl electrolyte solution.
**The resistance for this filter could not be calculated, but was assumed to be negligible and a value of 0? was used for purposes of this table.

Performance of a Filter-Enhanced Microfluidic Flowing Liquid Junction

Table 6 below provides experimental test data for flow cells (reference electrodes lacking a Ag/AgCl half-cell) having exemplary enhanced junction assemblies within the scope of the present invention. The material of the exemplary junction structures was obtained from Osmonics Laboratory Products (Westborough, Mass., USA), part No. AI54CL91I. Table 6 was generated based on the actual, experimentally determined data derived from enhanced junction assemblies using one or more filters in conjunction with a microfluidic flowing liquid junction structure such as those described above.

Experiment E-1007 was performed with a flow cell having a liquid junction structure matched with a suitable high flux, high capacity filtration member. The liquid Junction structure comprised an array of nanochannels, wherein the inner diameter of the nanochannels was approximately 231 nm and the length of the nanochannels was about 15 microns. The liquid junction structure had about $12.6 \times 10^3$ total nanochannels. The filtration member selected to work in conjunction with the liquid junction structure comprised nanochannels having an inner diameter of about 100 nm and a length of approximately 6 microns. The total number of nanochannels in the filtration member was approximately $12.6 \times 10^6$.

From the values of the parameters stated above, it follows that the total number of nanochannels in the filtration member was greater than the total number of nanochannels in the liquid junction structure by a factor of 1,000. The inner diameter of the nanochannels of the liquid junction structure was more than twice the size of the inner diameter of the nanochannels in the filtration member. The length of the nanochannels of the liquid junction structure was about 2.5 times larger than the corresponding length of the nanochannels of the filtration member.

Figure 18:
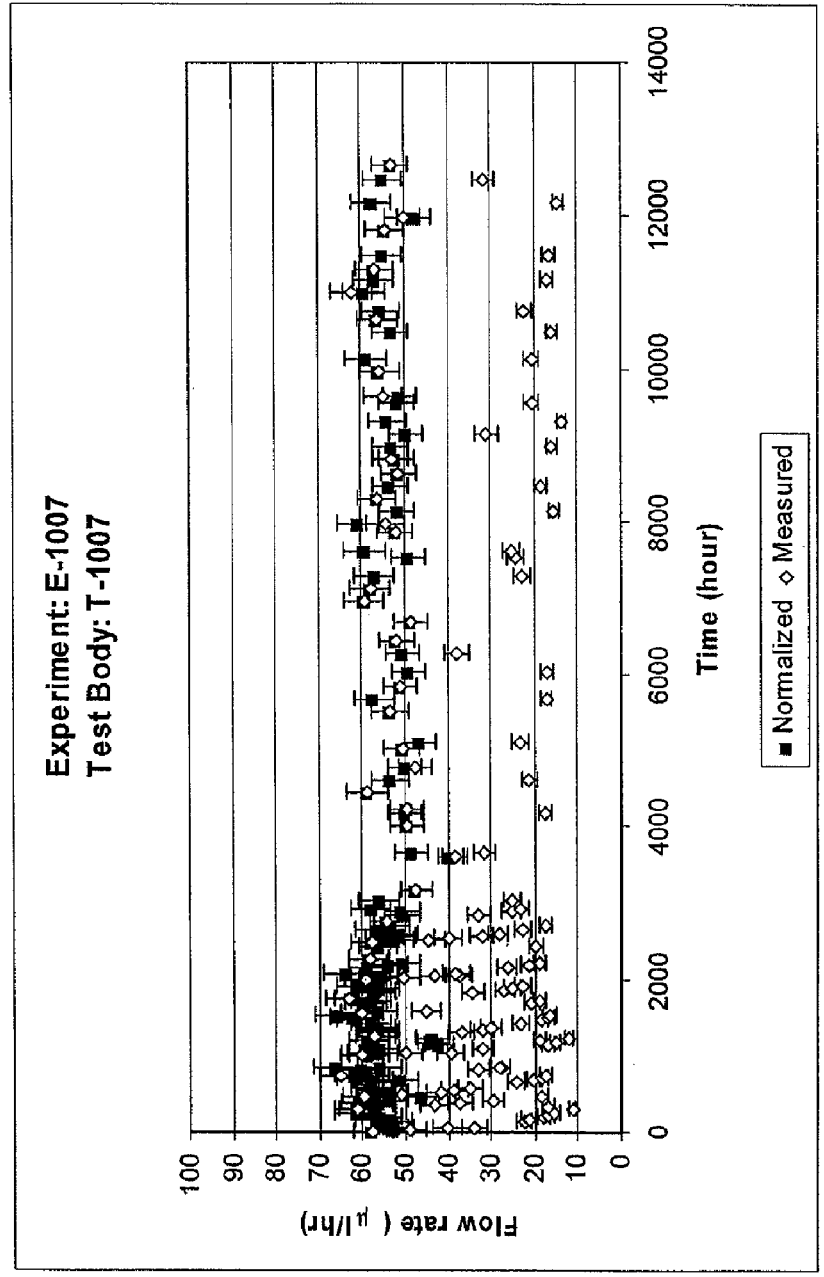
FIG. 18 depicts flow experiment E-1007 with a plot of both measured flow rate (μl/hr) data and normalized flow rate data as a function of total operational time for a flow cell using an enhanced junction assembly over a period of approximately 12,000 hours. These data were obtained using the first generation pressurized flow cell assembly designated T-1007. ◊: Measured flow rates, ■: Flow rates normalized to a constant 40 psig internal flow cell pressure.

Experiment E-1007 was performed at a pressure of 40 psig. The flow cell was tested for a period of approximately 6,000 hours (approximately nine months), and it exhibited a normalized average flow rate of 55 μL/hr. As is illustrated by FIG. 18, the electrolyte flow rate from the reference electrode remained substantially constant for over a period of at least approximately 6,000 hours.

Experiment E-1022 was performed with a flow cell having a liquid junction structure that comprised an array of nanochannels, wherein the inner diameter of the nanochannels was approximately 175 nm and the length of the nanochannels was about 6 microns. The liquid junction structure had about 600 nanochannels. Two filtration members were configured to work in conjunction with the liquid junction structure. Filtration member 1 had approximately $3.14 \times 10^6$ nanochannels, which had an average inner diameter of about 100 nm and a length of approximately 6 microns. Filtration member 2 had approximately $3.14 \times 10^6$ nanochannels, which had an inner diameter of about 200 nm and a length of approximately 6 microns.

The E-1022 experiment data illustrates that the total number of nanochannels of each of the filtration members was greater than the total number of nanochannels in the liquid junction structure by a factor of about 5,000. The inner diameter of the nanochannels of the liquid junction structure was twice the size of the inner diameter of the nanochannels of Filter 1, and about the same size as that of Filter 2. The length of the nanochannels of the liquid junction structure was about the same as the corresponding length of the nanochannels of each of the filtration members.

Figure 19:
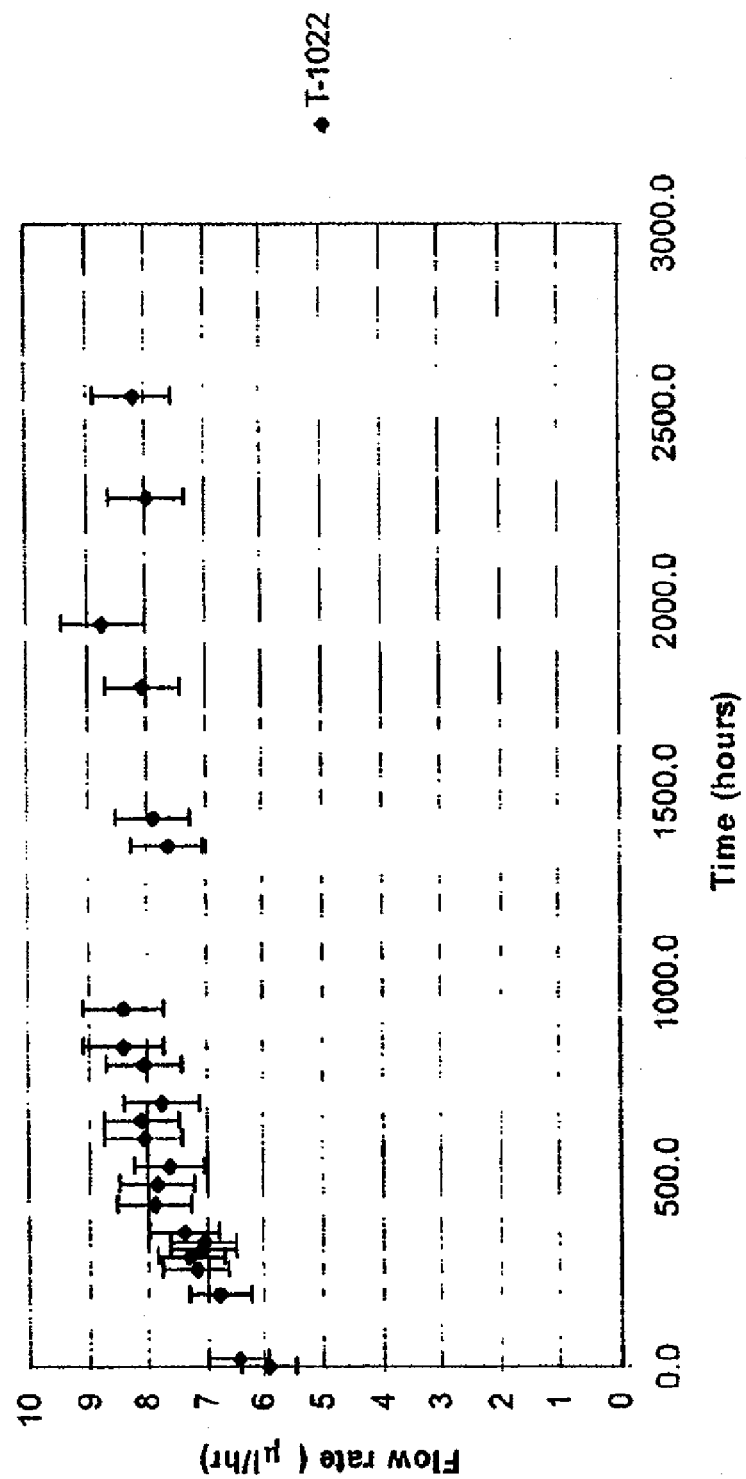
FIG. 19 depicts flow experiment E-1022 with a plot of measured flow rates (μl/hr) as a function of total operational time for pressurized flow cell assembly T-1022 with enhanced junction structure over a period of approximately 2500 hours (over three months). Internal pressure of the flow cell was kept at a constant 40 psig. Polycarbonate filter members having 200 and 100 nm pores were used to increase the longevity and stability of the junction array structure used in flow cell T-1022. The junction array structure nanochannels were etched to 175 nm i.d. and not coated with PVP.

Experiment E-1022 was performed at a pressure of 40 psig. The flow cell was tested for approximately 2,300 hours, and it exhibited a normalized average flow rate of about 8 μL/hr. FIG. 19 depicts a plot for Experiment E-1022. FIG. 19 shows that the flow cell using the filter-enhanced microfluidic flowing liquid junction exhibited a substantially constant electrolyte flow rate for at least about 2,500 hours of operation.

Experiment E-1010 was performed with a flow cell having a liquid junction structure matched with a suitable high flux, high capacity filtration member. The liquid junction structure comprised an array of nanochannels, wherein the inner diameter of the nanochannels was approximately 276 nm and the length of the nanochannels was about 15 microns. The liquid junction structure had about $12.6 \times 10^3$ total nanochannels. The filtration member comprised nanochannels having an inner diameter of 100 nm and a length of 6 microns. The total number of nanochannels in the filtration member was approximately $12.6 \times 10^6$.

The data of the E-1010 experiment show that the total number of nanochannels in the filtration member was greater than the total number of nanochannels in the liquid junction structure by a factor of 1000. The inner diameter of the nanochannels of the liquid junction structure was twice the size of the inner diameter of the nanochannels in the filtration member. The length of the nano channels of the liquid junction structure was about 2.5 times larger than the corresponding length of the nanochannels of the filtration member.

Experiment E-1010 was performed at a pressure of 40 psig. The flow cell was tested for approximately 1939 hours, and it exhibited a normalized average flow rate of 82 μL/hr.

Figure 20:
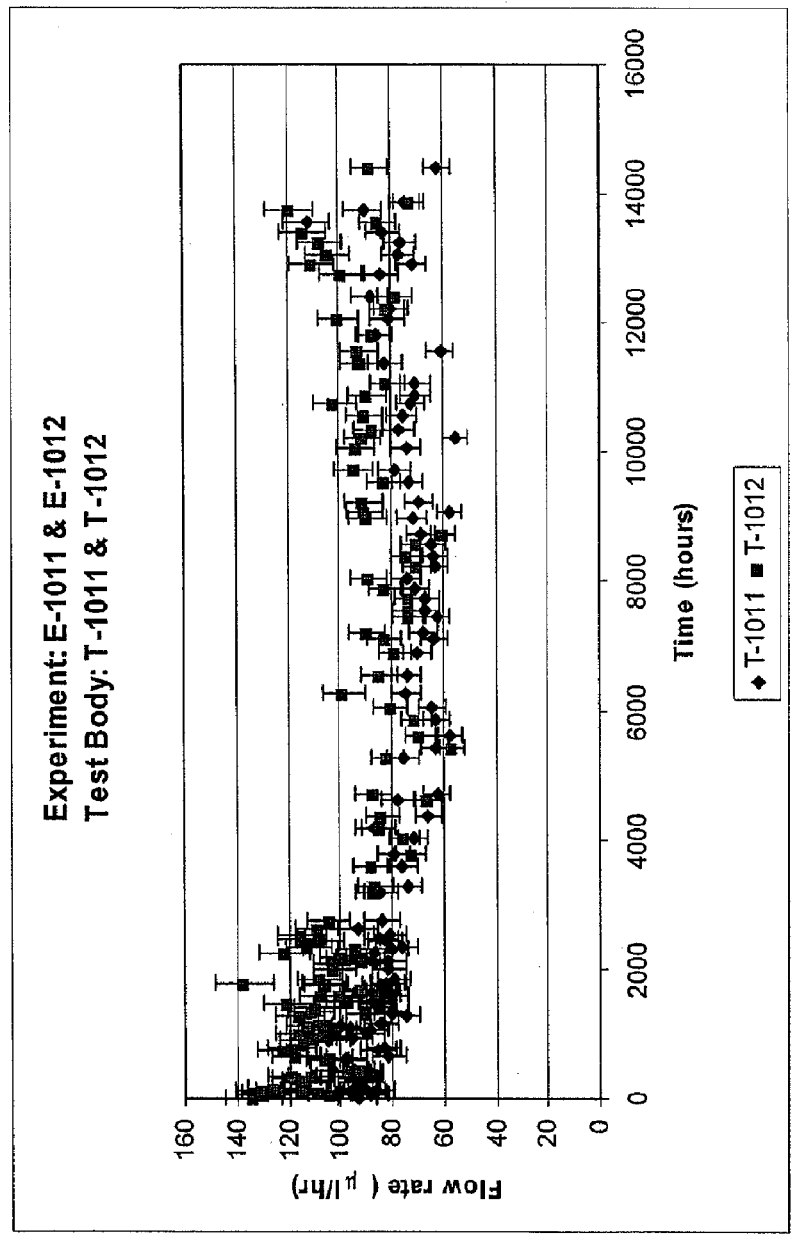
FIG. 20 depicts flow experiments E-1011 and E-1012 with a plot of normalized flow rates (μl/hr) as a function of total operational time for pressurized flow cell assemblies T-1011 and T-1012 with enhanced junction structures over a period of approximately 14,000 hours (about 7 months). Measured flow rate data were normalized to a constant 40 psig internal flow cell pressure. The junction structure of T-1011 was treated with PVP in the BJC lab. The junction structure of T-1012 was treated with PVP in the UCI cleanroom.
Figure 21:
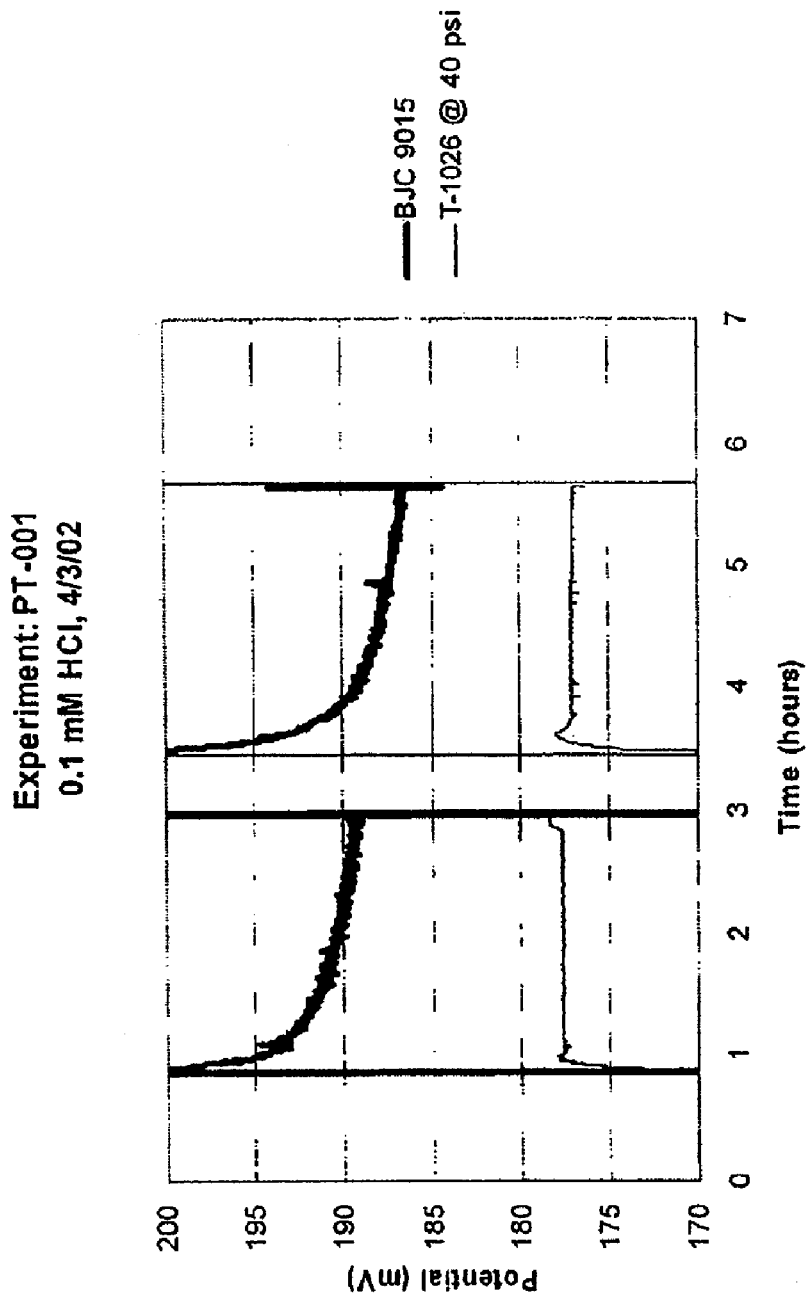
FIG. 21 depicts experiment PT-001 with a plot of the measured potential (mV) as a function of time (hours) for a reference electrode T-1026 with enhanced junction structure and for a diffusion junction reference electrode model number BJC 9015. Both reference electrodes were used with a common pH monoprobe to make potential measurements in 0.1 mM HCl after the electrodes had come to equilibrium in 7.00 buffer. The data show the T-1026 rapidly coming to a stable potential and maintaining that potential while the 9015 fails to achieve a stable potential in the same time span. The plot shows the T-1026, the 9015, and the pH monoprobe being immersed twice in the test solution during the course of the experiment.
Figure 22:
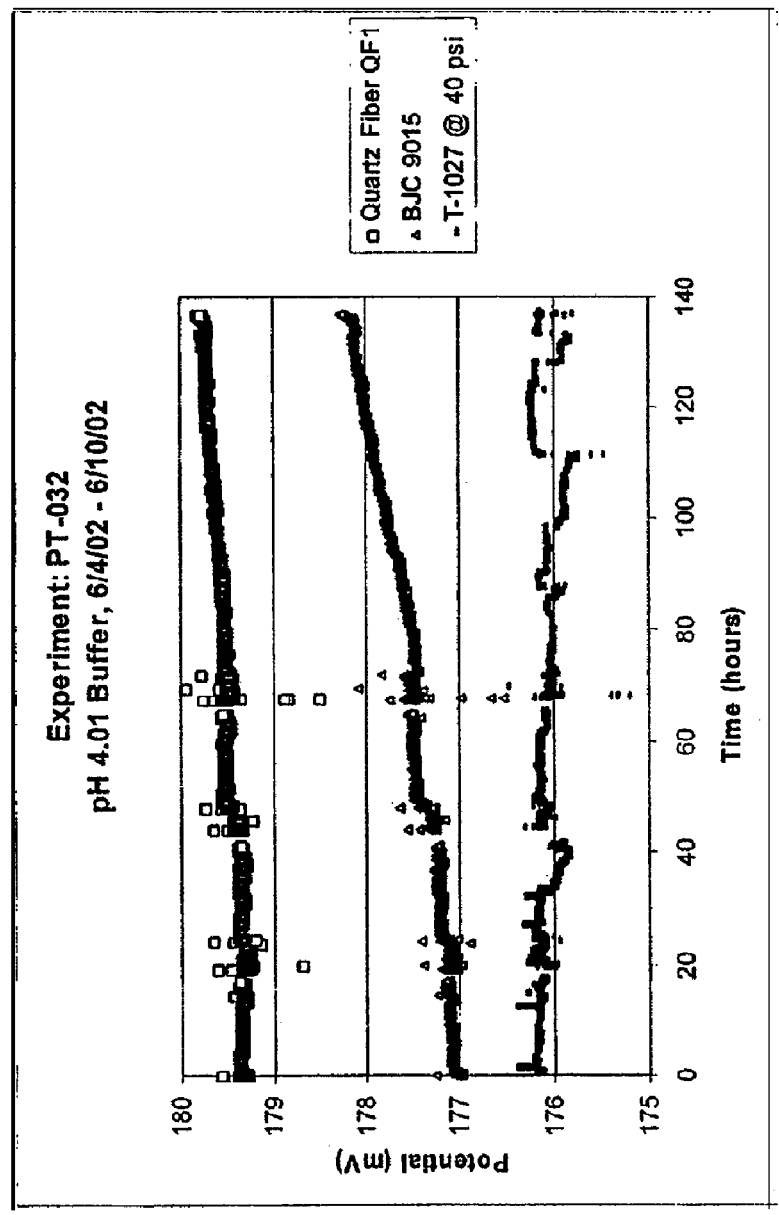
FIG. 22 depicts experiment PT-032 with a plot of the measured potential (mV) as a function of time (hours) for the pressurized reference electrode T-1027, a quartz fiber laboratory reference electrode QF1, and a diffusion junction reference electrode model number BJC 9015. All three reference electrodes were used with a common pH monoprobe to make potential measurements in pH 4.01 phthalate buffer over a period of about 140 hours. The data show both QF1 and the 9015 slowly drifting to a higher potential while the slope of the T-1027 data remains flat.
Figure 23:
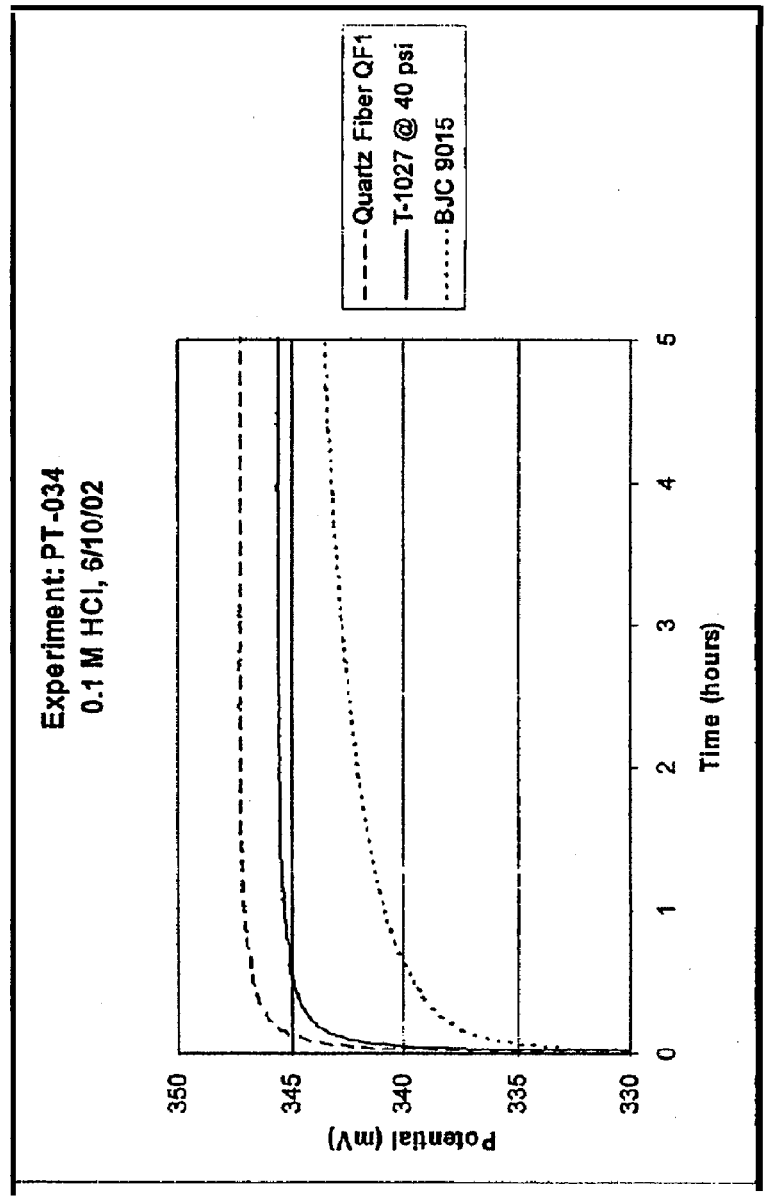
FIG. 23 depicts potential experiment PT-034 with a plot of the measured potential (mV) as a function of time (hours) for the pressurized reference electrode T-1027, for a quartz fiber laboratory reference electrode QF1, and for a diffusion junction reference electrode model number BJC 9015. All three reference electrodes were used with a common pH monoprobe to make potential measurements in 0.1 M HCl over a period of about 5 hours. The data show both the T-1027 and the research grade QF1 rapidly reaching a stable potential within the first hour of immersion in the test solution while the 9015 has not reached a stable potential after 5 hours of immersion.
Figure 24:
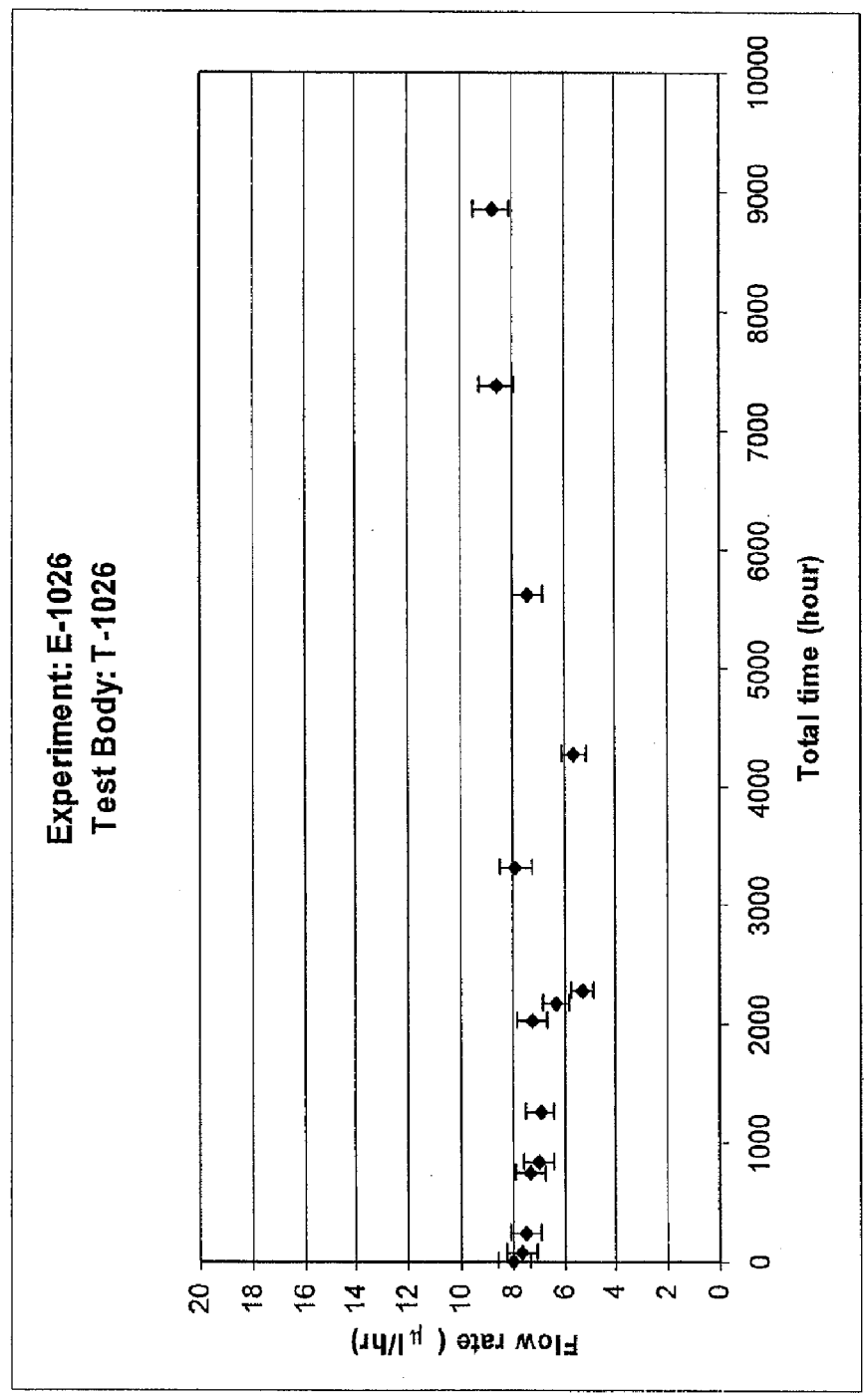
FIG. 24 depicts flow experiment E-1026 with a plot of measured flow rates as a function of total operational time for a pressurized reference electrode T-1026 with enhanced junction structure over a period of approximately 9,000 hours. Internal pressure of the flow cell was kept at a constant 40 psig. Polycarbonate filter members having 80 nm pores were used to increase the longevity and stability of the junction array structure used in reference electrode T-1026. The nominal diameters of the polyethylene junction array structure nanochannels are 100 nm.

The other experiments tabulated in Table 6 may be interpreted in a manner similar to the three experiments described so far. Additionally, FIG. 20 shows data plots for experiments E-1011 and E-1012, also presented in Table 6.

TABLE 6

| | Experiment number | | | | |
|---|---|---|---|---|---|
| | E1007 | E1009 | E1010 | E1011 | E1012 |
| Status | Active | Completed | Completed | Active | Active |
| Junction array: | | | | | |
| Channel length (μm) | 15 | 15 | 15 | 15 | 15 |
| Channel diameter (nm) | 231 | 261 | 276 | 261 | 285 |
| Total # of channels | $1.26 \times 10^4$ | $1.26 \times 10^4$ | $1.26 \times 10^4$ | $1.26 \times 10^4$ | $1.26 \times 10^4$ |
| Source | Osmonics | Osmonics | Osmonics | Osmonics | Osmonics |
| Filtration Member 1: | | | | | |
| Channel length (μm) | 6 | 6 | 6 | 6 | 6 |
| Channel diameter (nm) | 100 | 100 | 100 | 100 | 100 |
| Total # of channels | $1.26 \times 10^7$ | $1.26 \times 10^7$ | $1.26 \times 10^7$ | $1.26 \times 10^7$ | $1.26 \times 10^7$ |
| Source | Osmonics | Osmonics | Osmonics | Osmonics | Osmonics |
| Filtration Member 2: | | | | | |
| Channel length (μm) | | 60 | | | |
| Channel diameter (nm) | | 20 | | | |
| Total # of channels | | $1 \times 10^{11}$ | | | |
| Source | | Whatman | | | |
| Conditions: | | | | | |
| Initial pressure (psig) | 40 | 40 | 40 | 40 | 40 |
| Experiment duration (hours) | 5684 | 2808 | 1939 | 5275 | 5278 |
| Flow rate: | | | | | |
| Initial flow rate (μl/hr) | 58 | 94 | 118 | 94 | 134 |
| Final flow rate (μl/hr) | / | 50 | 46 | / | / |
| Max. flow rate (μl/hr) | 65 | 101 | 127 | 96 | 134 |
| Min. flow rate (μl/hr) | 11 | 67 | 10 | 24 | 24 |

TABLE 6-continued

| | | | | | |
|---|---|---|---|---|---|
| Average normalized flow rate (μl/hr) | 57 | 88 | 82 | 87 | 107 |
| Total flow volume (ml/mm$^2$) | 97 | 71 | 22 | 83 | 123 |

| | Experiment number | | | |
|---|---|---|---|---|
| | E1016 | E1018 | E1019 | E1022 |
| Status | Active | Completed | Active | Active |
| Junction array: | | | | |
| Channel length (μm) | 15 | 15 | 15 | 6 |
| Channel diameter (nm) | 280 | 284 | 280 | 175 |
| Total # of channels | 3.14 × 103 | 3.14 × 103 | 3.14 × 103 | 6.28 × 102 |
| Source | Osmonics | Osmonics | Osmonics | Osmo/BJC |
| Filtration Member 1: | | | | |
| Channel length (μm) | 6 | 6 | 6 | 6 |
| Channel diameter (nm) | 100 | 100 | 100 | 100 |
| Total # of channels | 3.14 × 106 | 3.14 × 106 | 3.14 × 106 | 3.14 × 106 |
| Source | Osmonics | Osmonics | Osmonics | Osmonics |
| Filtration Member 2: | | | | |
| Channel length (μm) | 60 | 60 | 60 | 6 |
| Channel diameter (nm) | 20 | 20 | 20 | 200 |
| Total # of channels | 1 × 1011 | 1 × 1011 | 1 × 1011 | 5.5 × 105 |
| Source | Whatman | Whatman | Whatman | Osmonics |
| Conditions: | | | | |
| Initial pressure (psig) | 40 | 40 | 40 | 40 |
| Experiment duration (hours) | 4846 | 1537 | 4440 | 3454 |
| Flow rate: | | | | |
| Initial flow rate (μl/hr) | 32 | 37 | 53 | 6 |
| Final flow rate (μl/hr) | / | 52 | / | / |
| Max. flow rate (μl/hr) | 44 | 54 | 63 | 9 |
| Min. flow rate (μl/hr) | 9 | 24 | 39 | 6 |
| Average normalized flow rate (μl/hr) | 27 | 41 | 51 | 8 |
| Total flow volume (ml/mm$^2$) | 117 | 81 | 250 | 25 |

Technical, Computational and Theoretical Analyses

Although the invention is not limited to any specific explanation of theory to explain why or under what conditions it performs as described herein, the following technical, computational and theoretical analyses are advanced to explain the invention.

The technical aspects of the microfluidic flowing liquid junction of the invention are addressed. The theoretical and practical requirements of a stable liquid junction are described, and the advantages of using a microfluidic flowing liquid junction are described and presented. Calculations and references demonstrate that the inventive use of microfluidic and nanopore technology lead to a stable liquid junction potential.

Potentiometric measurements are necessarily made using two electrodes. One electrode is the sensing electrode, which changes its potential with the concentration, or activity, of the analyte, e.g., $a_i$ in eq. (1). The other electrode is the reference electrode, which ideally generates a constant half-cell potential, $E_{ref}$, eq. (1). The potential at each electrode is characteristic of the physicochemical state of the electrode system, for example, the potential depends on temperature, pressure and the chemical composition of the system. The potential of the reference half-cell remains constant by placing the electrode in a separate compartment with its own electrolyte. The reference compartment has a conductive path to the sample solution. The arrangement of the electrode, the reference electrolyte and the conductive path is known as the reference electrode. See Midgley, K.; Torrance, K. *Potentiometric Water Analysis*, 2$^{nd}$ ed.; John Wiley & Sons: New York, 1991; p 12. The interface between the reference electrode and the sample solution is the liquid junction, which contributes a potential, $E_{junc}$. The sum of the sensing and reference electrode potentials, and the liquid junction potential is the measured cell potential, $E_{cell}$, eq. (1).

$$E_{cell} = \left(E_i^o + \frac{RT}{nF}\log a_i\right) + E_{ref.} + E_{junc.} \quad (1)$$

In order to determine the liquid junction potential accurately (see Bates, R. G. *The Determination of pH*; John Wiley and Sons: New York, 1973), or to minimize it (see Horvai, G.; Bates, R. G. *Anal. Lett.* 1989, 22, 1293), the overall composition of the sample must be known a priori. However, in most chemical analyses the desire is typically not to precisely determine or even minimize the liquid junction potential, but rather that the potential remain substantially constant and unchanging so that a reliable calibration can be made. There is typically no need to determine the liquid junction potential, but there is a need that the potential be substantially invariant from one test measurement to another at a given temperature and pressure. See IUPAC, Quantities, Units and Symbols in Physical Chemistry; Mills, I. Ed.; Blackwell: Oxford, 1993; p 62. Accurate potentiometric measurements thus depend on the constancy of the liquid junction potential. However, there is a fundamental limitation with the accuracy in potentiometric measurements due to a number of theoretical and practical limitations including a drifting, non-constant liquid junction potential.

The performance of a reference electrode not only depends on the chemical properties of the electrode, but also on the physical arrangement of the liquid junction. The four main physical criterion of substantially invariant liquid junction include, see Midgley, D.; Torrance, K. *Potentiometric Water Analysis*, 2$^{nd}$ ed.; John Wiley and Sons: New York, 1991; p 46, (i) the junction structure should be constant, (ii) stirring or streaming of the sample solution should not affect the reference potential, (iii) particulate matter from the sample should not clog the junction, and (iv) solution from one sample should not be retained in the junction and carried over to the next sample. The accuracy of any potentiometric measurement thus depends on the ability of the liquid junction design to meet these requirements.

Currently commercially available reference electrodes use an assortment of liquid junction structures and designs to protect the reference electrolyte from the sample. These materials include porous ceramic, porous Teflon, wood, asbestos, and various fibers. Designs with double junctions, glass-sleeves, and fused salts are also used. All these materials and designs are meant to keep the reference environment constant. However, even if the reference solution remains unchanged, the liquid junction can become contaminated with the sample solution. This inevitably alters the potential of the liquid junction, and requires the electrochemical sensor to be recalibrated. A changing liquid junction is typically why an electrochemical sensor requires frequent recalibration.

The most stable, reproducible, and reliable reference electrode designs incorporate a flowing-liquid junction. See Covington, A. K.; Whalley, P. D.; Davison, W. *Anal. Chim. Acta* 1985, 169, 221; Illingworth, J. A. *Biochem. J.* 1981, 195, 259; Wu, Y. C.; Feng, D.; Koch, W. F. J. *Solution Chem.* 1989, 18, 641; Ito, S.; Kobayashi, F.; 1 Baba, K.; Asano, Y.; Wada, H. *Talanta* 1996, 43, 135; Peters, G. *Anal. Chem.* 1997, 69, 2362; Lvov, S. N.; Zhou, X. Y.; Macdonald, D. D. *J. Electroanal. Chem.* 1999, 463, 146; Brezinski, D. P. *The Analyst* 1983, 108, 425. The constant flow of reference electrolyte through the liquid junction helps it maintain a constant composition by the continual renewal of fresh electrolyte. The disadvantage of using such an electrode is that it requires considerable maintenance because the reference cell must be frequently refilled with electrolyte. For this reason, flowing junctions are usually only suitable for the laboratory environment. Another problem of a typical flowing-reference electrode is that if the sample is at a pressure higher than the reference reservoir, the reference cell will readily become contaminated with the sample. Because of these disadvantages, in recent years, the convenience and low maintenance of diffusion-style junctions has replaced the flowing-liquid junction in industrial application.

A superior flowing-liquid junction has been developed by combining microfluidic materials and nanomaterials. The electrolyte has a continual flow of small, manageable volumes of electrolyte through the junction with a linear velocity sufficient to eliminate contamination of the junction and/or contamination of the reference electrolyte. The microfluidic flowing liquid junction provides the superior stability and performance of a flowing liquid junction yet remain maintenance-free for extended periods of time, including a week, two weeks, a month, six months, a year, or two years.

When miniaturizing chemical and physical processes, as in microfluidics, scaling laws must be considered. In addition, modeling fluid mechanics requires that correct assumptions as to the type of flow be made. Microfluidics typically have very low Reynolds numbers, Re<1, see Madou, M. *Fundamentals of Microfabrication*; CRC Press: New York, 1997; p 429, where viscous forces dominate. A consequence of viscous flow is that each microscopic fluid element follows a fixed path or streamline. Any subsequent fluid element, starting at the same point, will follow the same streamline along its entire course. See Giddings, J. C. *Unified Separation Science*; John Wiley and Sons: New York, 1991; pp. 58-63. Such a flow pattern creates a reproducible, non-varying, and predictable structure, like that desired in a flowing-liquid junction. To characterize the flow through a liquid junction the velocity profiles must be determined.

To determine the velocity profile through a microchannel or nanochannel, all of the external forces acting on the fluid are to be balanced. First, the Newtonian acceleration (or inertial) forces are significant for only a brief moment before steady flow is achieved in very small channels, see Giddings, J. C. *Unified Separation Science*; John Wiley and Sons: New York, 1991; pp. 58-63, and can be neglected. Second, all of the fluidic elements under consideration terminate as a sudden expansion. This implies that the kinetic energy of the fluid is not transferred from one element to the next. See Gravesen, P.; Branebjerg, J.; Jensen, O, S. *J. Micromech. Microeng.* 1993, 3, 168. Third, in very small channels gravitational forces may be neglected since the pressure required to induce steady flow is typically much larger than the gravitational force, i.e., $\Delta p \gg \rho gh$. See Giddings, J. C. *Unified Separation Science*; John Wiley and Sons: New York, 1991; pp. 58-63. By neglecting acceleration, kinetic, and gravitational forces we need only balance the pressure acting against the viscous forces in order to determine the velocity profile through a microchannel. Flow through very small channels is described by the Hagen-Poiseuille equation, eq. (2). The flux, Q (L/s), or the rate of flow through a cross-sectional area of a single channel, is a function of the channel dimensions, the differential pressure, and the properties of the solution.

$$Q = \frac{\pi \Delta p r_o^4}{8L\eta} \tag{2}$$

In eq. (2) $\Delta p$ is the pressure differential at the two ends of the channel, $r_o$ and L are the radius and length of the channel, respectively, and $\eta$ is the solution viscosity. (All of the calculations in this proposal have assumed that the viscosity of the electrolyte is equal to 1.0 cp.) See All pure aqueous KCl solutions have a viscosity between 0.9 and 1.1 cp. Hai-lang, Z.; Shi-Jun, H. *J. Chem. Eng. Data* 1996, 41, 516. Examination of eq. (2) indicates that $Q \propto r_o^4$, thus, simply constricting the cross section of a channel will greatly diminish the flow through it. However, decreasing the cross-sectional area of a channel increases the electrolytic resistance. The conductance through a cylindrical channel can be calculated by using eq. (3).

$$G = \frac{1}{R} = \frac{\lambda C \pi r_o^2}{L} \tag{3}$$

The electrolytic resistance of the channel is taken as the reciprocal of the cell conductance, G. $\lambda$ is the equivalent ionic conductance, C is the electrolyte concentration, A and L are the cross-sectional area and length of the channel, respectively. $\lambda$ for a 4.0 M KCl solution is $\sim 10^{-2}$ m$^2$ S mol$^{-1}$. See *Handbook of Chemistry and Physics*, 71$^{st}$ ed.; Lide, D. R., Ed.; CRC Press: Ann Arbor, 1990. To minimize the electrolyte flow-rate and the electrolytic resistance by simply reducing the size of a single channel is impractical, since the electrolytic resistance rapidly becomes too high when the channel radius<~1 μm. For example, the calculated electrolytic resistance, using eq. (3), of a 1-mm long channel with a 1-μm radius containing 4.0 M KCl is ~8 MΩ. This resistance is higher than is conventionally believed to produce acceptable results with typical commercial instrumentation. Fortunately, flow decreases as the fourth power of the radius while resistance increases as the square of the radius. Decreasing channel cross section but increasing the number of channels is a practical way to reduce the electrolytic resistance while maintaining the desired low flow.

Preferred embodiments of the present invention use an array of nanochannels as a liquid junction structure to minimize both the flow rate and electrolytic resistance. For example, while a single nanochannel with a 5 nm radius and a 6 μm length (see Nishizawa, M.; Menon, V. P.; Martin, C. R. Science 1995, 268, 700) has a theoretical electrolytic resistance of about 1,000 MΩ in 4.0M KCl (eq. (3)), an array having $10^5$ nanochannels—each nanochannel having a 5 nm radius and a 6 μm length—will have a theoretical electrolytic resistance of less than 100 kΩ.

Calculations thus far show that a microfluidic flowing liquid junction can provide the desired flow control and electrolytic conductivity to achieve a commercial product. Next, the electrolyte velocity needed to minimize the back diffusion of a sample into the liquid junction is calculated. The average solution velocity through a single nanochannel can be calculated by dividing the flux, Q, eq. (2), by the cross-sectional area of the nanochannel.

$$v = \frac{Q}{\pi r_o^2} \quad (4)$$

Figure 12:
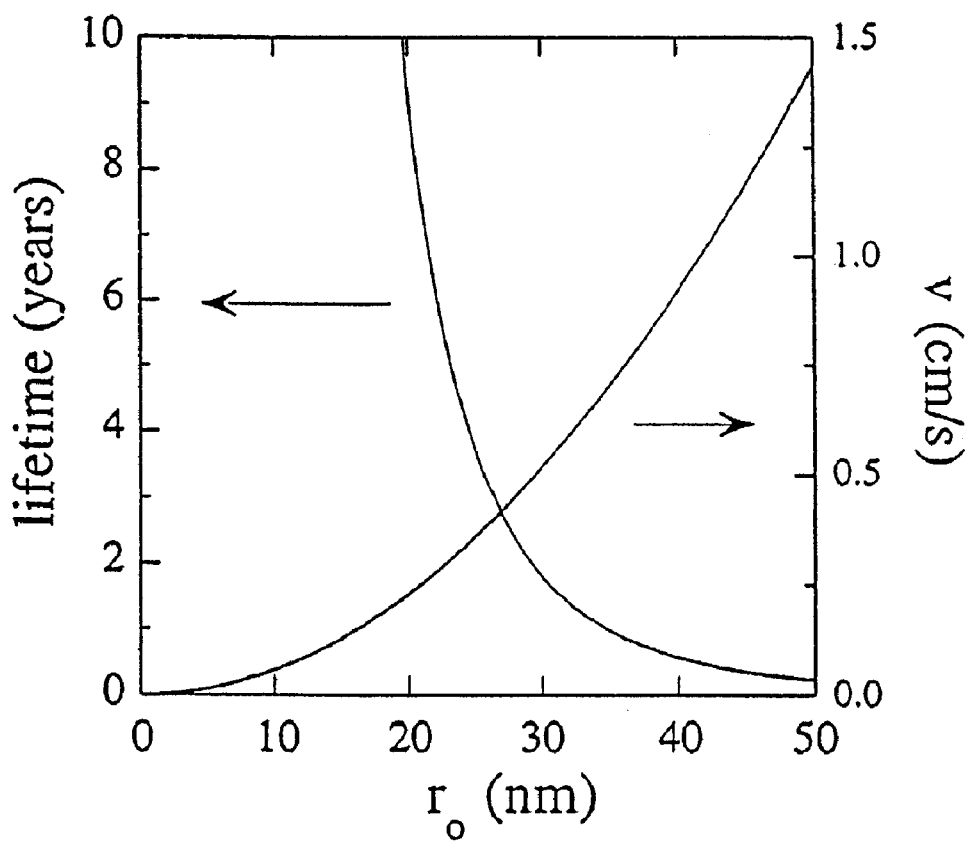
FIG. 12 is a plot of the flux (linear flow) through a nanochannel array and the average velocity (v) through a single nanochannel as a function of the effective radius of the nanochannel.
Figure 13:
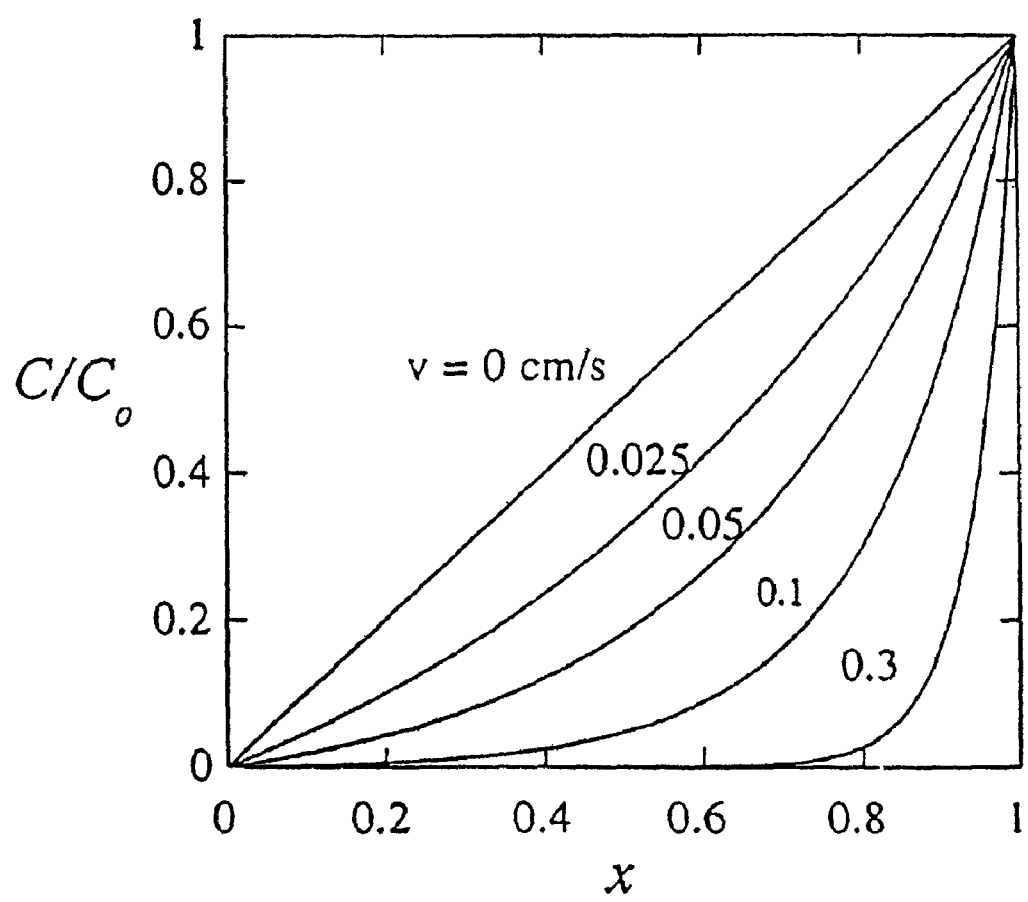
FIG. 13 is a set of concentration profiles in a liquid junction, plotted as a function of velocity, and as described in Equation (7).

Using eqs. (2) and (4), the flux through a nanochannel array and the average velocity (v) through a single nanochannel are plotted in FIG. 12 as a function of the nanochannel radius. The calculations assume a steady pressure difference of 40 psi. The flux is plotted as the sensor life assuming a 50 ml reservoir of electrolyte. The array contains $10^5$ nanochannels and is 6 μm long. A 50 ml reservoir will be sufficient for continuous operation of a year or more for nanochannel radii less than approximately 30 nm. The radii of the nanochannels or microtubes may also have radii of less than approximately 20 nm, less than approximately 40 nm, less than approximately 50 nm, or less than approximately 60 nm. By increasing the volume of the reservoir, or by decreasing the number or density of the nanochannels, the lifetime of a sensor can be adjusted as needed, as will be appreciated by those of ordinary skill in the art.

An order of magnitude estimate of the electrolyte velocity needed to diminish diffusion of the sample into the liquid junction is calculated. A hydrodynamic model is used to model the convective-diffusion transport through a nanochannel. This model neglects electrostatic interactions and migrational effects. Diffusion of the sample into the liquid junction is described by Fick's first law, $N_D = -D\nabla C$, and the convective flux is $N_v = Cv$. The sum of the diffusional and convective fluxes is the total flux, eq. (5).

$$N = -D\frac{dC}{dx} + Cv \quad (5)$$

In eq. (5) C is the concentration of the sample at position x in the channel. v is the convective velocity of the electrolyte solution, and is approximated as the average solution velocity through the channel. Integration of the continuity equation, $\nabla \cdot N = 0$, with boundary conditions, $C = C_o$ at $x = l$ and $C = 0$ at $x = 0$, where $C_o$ is the initial concentration of the sample, and l is the length of the nanochannel, yields the concentration profile for convective-diffusion through a nanochannel.

$$\frac{C}{C_o} = \frac{\exp\left(\frac{vx}{D}\right) - 1}{\exp\left(\frac{vl}{D}\right) - 1} \quad (6)$$

Preferred Laboratory System Embodying the Invention

A system according to a preferred embodiment of the invention was assembled. This system was used to test electrodes at controlled temperatures, pressures and agitation rates. The system consists of a 50 ml pressure cell, which can handle pressures as high as 45 psig as equipped. The laboratory test system mimics the different, sometimes harsh environments to which sensors may routinely be exposed in industrial or field applications. The cell is exposed to temperatures for example, within 0.1° C., in a precision temperature bath. A mechanical stirrer provides adequate agitation and mixing of the test solution. All of the instrumentation is linked to a computer for data acquisition and archiving of the experimental measurements.

Theoretical Aspects of the Preparation and Characterization of the Nanochannel Array The Au nanochannel arrays that were used as the liquid junction structure were prepared via a general approach for preparing nanomaterials called "template synthesis." See Hulteen, J. C.; Martin, C. R. J. Mater. Chem. 1997, 7, 1075. The template method entails the synthesis of a desired material within the channels of a microporous membrane. The membranes employed have cylindrical channels with monodisperse diameters that run the complete thickness of the membrane. Corresponding cylindrical nanostructures of the desired material are obtained within the channels.

A commercially available microporous polycarbonate filtration membrane may be used as the template to prepare the nanochannel arrays. This membrane contains monodisperse and cylindrical pores. An electronic plating procedure is used to deposit Au nanochannels within these pores. See Nishizawa, M.; Menon, V. P.; Martin, C. R. Science 1995, 268, 700; Hulteen, J. C.; Martin, C. R. J. Mater. Chem. 1997, 7, 1075; Hulteen, J. C.; Martin, C. R. J. Am. Chem. Soc. 1998, 26, 6603; Menon, V. P.; Martin, C. R. Anal. Chem. 1995, 67, 1920. This Au plating procedure is well known in the art.

The template membrane may be first rinsed in methanol and then immersed in a 0.025 M $SnCl_2$ and 0.07 M in trifluoroacetic acid solution. This results in "sensitization" of the membrane, typically meaning the adsorption of Sn(II) to the channel walls and membrane surfaces. The sensitized membrane is then immersed into an aqueous solution of ammoniacal $AgNO_3$. This causes the following surface redox reaction, $$2Ag^+ + Sn(II) \rightarrow 2Ag^° + Sn(IV) \quad (7)$$

and the channel walls and membrane phases become coated with nanoscopic Ag particles. These particles act as the initial catalyst for electroless Au deposition. Finally, the membrane may be placed in a gold plating bath, which contains 0.5 ml of a commercially-available gold plating solution, 0.127 M $Na_2SO_3$, 0.625 M formaldehyde and 0.025 M $NaHCO_3$. The solution may be adjusted to pH 10 by dropwise addition of 0.5 M $H_2SO_4$. The temperature of this plating bath is typically maintained at 5° C. The inside diameter of the Au nanochannels deposited within the pores of the array is adjusted by varying the plating time, which typically refers to the immersion time in the Au plating bath.

This procedure is optionally used to prepare arrays containing Au nanochannels with inside diameters of molecular dimensions (<1 nm). See Nishizawa, M,; Menon, V. P.; Martin, C. R. *Science* 1995, 268, 700; Hulteen, J. C.; Martin, C. R. *J. Mater. Chem.* 1997, 7, 1075; Hulteen, J. C.; Martin, C. R. *J. Am. Chem. Soc.* 1998, 26, 6603; Menon, V. P.; Martin, C. R. *Anal. Chem.* 1995, 67, 1920; Petzny, W. J.; Quinn, J. A. *Science* 1969, 166, 751. Ion-transport in these arrays has been studied, see Nishizawa, M,; Menon, V. P.; Martin, C. R. *Science* 1995, 268, 700. The resulting nanochannels are ion permselective and may be reversibly switched between anion-transporting and cation-transporting states.

The inside diameters of the Au nanochannels may be readily approximated by measuring the flux of $H_2$ gas across the nanochannel array. See Petzny, W. J.; Quinn, J. A. *Science* 1969, 166, 751. See also Liu, C., Texas A&M University, College Station; 1991. The nanochannel samples are then placed in a vacuum oven for at least 12 hours prior to making the flux measurements, to remove traces of water or other volatile species absorbed in the nanochannels. Reproducible values of flux are best obtained when nanochannels are pretreated in this manner. The nanochannel array may then be placed in the gas-permeation cell, and the upper and lower half-cells evacuated. The upper half is pressurized to 20 psig with $H_2$, and the pressure-time transient associated with leakage of $H_2$ through the nanochannels into the lower half-cell was measured. This is converted to the flux of gas, from which the average nanochannel diameter may be approximated. Assuming gas-transport through a nanochannel array occurs via Knudsen diffusion, the flux of gas, $Q_{gas}$ (moles cm$^{-2}$ s$^{-1}$), is related to the pore density, n (pores cm$^{-2}$), the pore diameter, d (cm), and the membrane thickness, L (cm) using eq. (8):

$$(gas)_Q = \frac{8\pi n d^3 \Delta p}{3MRTL} \quad (8)$$

$\Delta p$ is the pressure difference across the membrane (dynes cm$^{-2}$), M is the molecular weight of the gas, R is the gas constant (erg K$^{-1}$ mol$^{-1}$), and T is the temperature (K). In our experiment, we know all of the parameters in eq. (8), except d.

A variety of nanochannel arrays of various sizes and materials may be constructed and used. These include different radii for example, (10, 20, 30 and 40 nm), and substrate materials, for example, (polycarbonate and polyester), and two Au surfaces. The inside diameter of the nanochannels may be varied by the plating time, which have been characterized for precise nanochannel dimensions. Au nanochannels and Au nanochannels with an adsorbed propanethiol monolayer are preferred. Chloride ions readily adsorb on gold surfaces, thus, in 4.0 M KCl reference solutions the Au nanochannels will have a net negative charge. However, the nanochannels pretreated with propanethiol have an inert, uncharged monolayer that prevents chloride ions from adsorbing.

Alternatively, addition of a propanthiol monolayer is accomplished by immersing the array into an ethanol solution containing the thiol. This small thiol molecule does not appreciably change the nanochannel inside diameter when the diameter>~5 nm. For this reason, there is no need to redetermine the nanochannel inside diameter after chemisorption of the thiol. In addition, the propanethiol-modified Au nanochannels remain water "wetable" after addition of the thiol. See Nishizawa, M,; Menon, V. P.; Martin, C. R. *Science* 1995, 268, 700.

Theoretical Discussion of Low Resistance Filtration Members Used in Conjunction with a Liquid Junction Structure in the Enhanced Junction Assemblies Flux capacity of the filter member is proportional to the reciprocal of the resistance of the filter member. Accordingly, the electrolytic resistance is an excellent comparative measure of the flux capacity of the filter members and of the junction array structures. Electrolytic resistance measurements are used to judge the suitability of the use of a filter member with a particular junction array structure.

The resistance of the filter member should be equal to or less than the resistance of the junction array so that the junction array always determines the volumetric flow rate through the enhanced microfluidic liquid junction structure. Preferably, the filter member will have a resistance that is much less than that of the junction structure. Selection of a suitable filter member or multiple filter members for use with a certain junction array structure can be made by comparative electrolytic resistance measurements. The sum of the resistances of the filter members preferably should be much less than the resistance of the junction array structure.

With reference to FIG. 14, the total electrolytic resistance across the liquid junction can be defined as the sum of the resistances of the filtration members 202, 202', and 202" added to the resistance of the microfluidic flowing liquid junction 204. This can be expressed by the following equation:

$$R_{total} = \Sigma_i R_i + R_j \quad (9)$$

where $R_j$ is the resistance of the liquid junction structure and $\Sigma_i R_i$ is the cumulative resistance across the filters 202, 202', and 202", where $R_i$ is the resistance of an individual filtration member, e.g., filter 202.

The resistance of an individual filtration member 202 or junction structure 204 is given by $$R_i = \frac{L}{\lambda CA} = \frac{L}{\lambda Cn\pi r^2} \quad (10)$$

where L is the length of the filter member or junction structure, $\lambda$ is the equivalent ionic conductance, C is the electrolyte concentration, and A is $n\pi r^2$, which is the total open area of the anisotropic filter member or junction structure.

The electrolytic resistance is related to the flux of electrolyte through an anisotropic structure using the following equation.

$$Q = \left(\frac{1}{R_i}\right)\left(\frac{r^2 \Delta p}{8\eta C \lambda}\right) \quad (11)$$

The variables in eq. (11) are listed and defined in the descriptive text following eqs. (2), (3), and (10).

As explained above, preferably the liquid junction structure 204 is the only structure that limits the volumetric flow rate (flux) of electrolyte exiting the reference electrode; hence, the filtration member 202 is capable of allowing a flow rate that is greater than or equal to the flow rate associated with the liquid junction structure 204. Expressing this in resistance, it is preferable that $$R_j \geq \Sigma_i R_i \quad (12).$$

Since particulates in the electrolyte eventually clog some of the pores of the filtration members 202, 202', and 202", it is preferred that $$R_j \gg \Sigma_i R_i \qquad (13).$$

The various articles of the scientific and/or medical literature, and the U.S. and international and/or foreign patents and patent applications cited herein are hereby incorporated by reference to the extent permitted by law. To the extent that each is incorporated by reference herein, each constitutes a part of the disclosure of this specification. Furthermore, specific embodiments, working examples, and prophetic examples of the invention have been described in detail to illustrate the broad applicability and principles underlying the invention, such as the use of microfluidic flowing liquid junction as part of a reference electrode or as part of a combination electrode, and the various methods of manufacturing and/or using the microfluidic flowing liquid junction, or of manufacturing and/or using a reference electrode or a combination electrode comprising a microfluidic flowing liquid junction. Notwithstanding these specific embodiments, working examples, and prophetic examples, it will be understood by those of skill in the art that the invention may be embodied otherwise without departing from such broad applicability and principles.

What is claimed is:

1. A flowing junction reference electrode comprising:
a microfluidic liquid junction member situated between a pressurized reference electrolyte solution and a sample solution, the junction member comprising fewer than approximately 100,000 discrete nanochannels; and
a filter member comprising a plurality of pores, wherein the diameter of any one pore is less than the diameter of any one nanochannel, and wherein the filter member is adapted to allow flow of the electrolyte solution through the filter member and into the junction member.

2. The electrode of claim 1, wherein the junction member comprises greater than approximately 10 nanochannels and less than approximately 10,000 nanochannels.

3. The electrode of claim 2, wherein the junction member comprises less than approximately 100 nanochannels.

4. The electrode of claim 1, wherein the nanochannels are substantially straight and substantially parallel to one another.

5. The electrode of claim 1, wherein the width of any one nanochannel is substantially equal to the width of any other nanochannel.

6. The electrode of claim 1, wherein the nanochannels have widths of greater than approximately 1 nanometer and less than approximately 900 nanometers.

7. The electrode of claim 1, wherein the nanochannels have widths of greater than approximately 100 nanometers and less than approximately 500 nanometers.

8. The electrode of claim 1, wherein the filter member comprises a plurality of pores, and wherein the pores are substantially straight and substantially parallel to one another.

9. The electrode of claim 1, wherein the filter member is configured to permit a volumetric flow of electrolyte solution through the filter member that is approximately equal to or greater than the volumetric flow capacity of the junction member.

10. The electrode of claim 1, wherein the nanochannels are coated.

11. The electrode of claim 1, wherein the junction member comprises a polymer selected from the group consisting of polycarbonate and polyimide.

12. The electrode of claim 1, wherein the junction member comprises a material selected from the group consisting of silicon, glass, and ceramic.

13. The electrode of claim 1, further comprising means for maintaining positive linear flow of the electrolyte solution through the nanochannels and into the sample solution.

14. The electrode of claim 13, wherein the means for maintaining positive linear flow of the electrolyte solution through the nanochannels and into the sample solution is selected from the group consisting of a pressurized collapsible bladder, an electro-osmotic pump, a mechanical pump, a piezoelectric pump, and a electro-hydrodynamic pump.

* * * * *

UNITED STATES PATENT AND TRADEMARK OFFICE
CERTIFICATE OF CORRECTION

PATENT NO. : 8,048,278 B2  
APPLICATION NO. : 11/925658  
DATED : November 1, 2011  
INVENTOR(S) : Broadley et al.

Page 1 of 1

It is certified that error appears in the above-identified patent and that said Letters Patent is hereby corrected as shown below:

In column 6 at line 40, change "second," to --second;--.

In column 7 at line 36, change "planar" to --planar,--.

In column 11 at line 18, change "Junction" to --junction--.

In column 12 at line 33, change "mm." to --nm.--.

In column 16 at line 16 (approx.), change "Furthermore" to --Furthermore,--.

In column 17 at line 19, change "propanetbiol" to --propanethiol--.

In column 26 at line 64 (approx.), change "KNSCP01300." to --KN5CP01300.--.

In column 34 at line 54, change "Junction" to --junction--.

In column 36 at line 26, change "nano channels" to --nanochannels--.

In column 37 at line 55, change "$E_{ref}$," to --$E_{ref.}$,--.

In column 38 at line 36, change "$E_{junc}$," to --$E_{junc.}$,--.

In column 40 at line 17 (approx.), change "O, S." to --O. S.--.

Signed and Sealed this  
Ninth Day of October, 2012

David J. Kappos  
*Director of the United States Patent and Trademark Office*